US010582870B2

(12) United States Patent
Allavatam et al.

(10) Patent No.: US 10,582,870 B2
(45) Date of Patent: Mar. 10, 2020

(54) METHODS AND DEVICES THAT IDENTIFY OVERDETECTION IN IMPLANTABLE CARDIAC SYSTEMS

(71) Applicant: CAMERON HEALTH, INC., St. Paul, MN (US)

(72) Inventors: Venugopal Allavatam, Saratoga, CA (US); Jay A. Warren, San Juan Capistrano, CA (US); Rick Sanghera, San Clemente, CA (US)

(73) Assignee: CAMERON HEALTH, INC., St. Paul, MN (US)

(*) Notice: Subject to any disclaimer, the term of this patent is extended or adjusted under 35 U.S.C. 154(b) by 164 days.

(21) Appl. No.: 15/948,476

(22) Filed: Apr. 9, 2018

(65) Prior Publication Data

US 2018/0220916 A1 Aug. 9, 2018

Related U.S. Application Data

(63) Continuation of application No. 13/214,099, filed on Aug. 19, 2011, now Pat. No. 9,962,100.

(60) Provisional application No. 61/375,732, filed on Aug. 20, 2010.

(51) Int. Cl.
*A61B 5/042* (2006.01)
*A61B 5/00* (2006.01)
*A61N 1/362* (2006.01)

(52) U.S. Cl.
CPC ............ *A61B 5/0422* (2013.01); *A61B 5/686* (2013.01); *A61B 5/7282* (2013.01); *A61N 1/3621* (2013.01)

(58) Field of Classification Search
CPC ..... A61B 5/0422; A61B 5/686; A61B 5/7282; A61N 1/3621
See application file for complete search history.

(56) References Cited

U.S. PATENT DOCUMENTS

| | | | |
|---|---|---|---|
| 6,393,316 B1 | 5/2002 | Gillberg et al. | |
| 6,754,528 B2 | 6/2004 | Bardy et al. | |
| 7,248,921 B2 | 7/2007 | Palreddy et al. | |
| 7,330,757 B2 | 2/2008 | Ostroff et al. | |
| 9,962,100 B2* | 5/2018 | Allavatam | A61B 5/0422 |
| 2003/0204215 A1 | 10/2003 | Gunderson et al. | |
| 2004/0254611 A1 | 12/2004 | Palreddy et al. | |
| 2004/0254613 A1 | 12/2004 | Ostroff et al. | |
| 2006/0167503 A1 | 7/2006 | Warren et al. | |
| 2009/0187227 A1 | 7/2009 | Palreddy et al. | |
| 2009/0198296 A1 | 8/2009 | Sanghera et al. | |
| 2009/0228057 A1 | 9/2009 | Allavatam et al. | |
| 2009/0259271 A1 | 10/2009 | Allavatam et al. | |
| 2010/0004713 A1 | 1/2010 | Warren et al. | |
| 2010/0094369 A1 | 4/2010 | Allavatam et al. | |
| 2010/0331904 A1 | 12/2010 | Warren et al. | |

(Continued)

*Primary Examiner* — Lindsey G Wehrheim
(74) *Attorney, Agent, or Firm* — Seager, Tufte & Wickhem LLP

(57) ABSTRACT

Methods, systems, and devices for signal analysis in an implantable cardiac device such as an implantable cardioverter defibrillator. In illustrative examples, captured data including detected events is analyzed to identify likely overdetection of cardiac events. Analysis of the apparent width of detected events is used to determine whether overdetection is occurring. If overdetection is identified, data may be modified to correct for overdetection, to reduce the impact of overdetection, or to ignore overdetected data.

20 Claims, 15 Drawing Sheets

(56) References Cited

U.S. PATENT DOCUMENTS

2011/0098585 A1 4/2011 Warren et al.
2011/0098775 A1 4/2011 Allavatam et al.

* cited by examiner

METHODS AND DEVICES THAT IDENTIFY OVERDETECTION IN IMPLANTABLE CARDIAC SYSTEMS

CROSS REFERENCE TO RELATED APPLICATIONS

The present application is a continuation of U.S. application Ser. No. 13/214,099, filed Aug. 19, 2011, which claims the benefits of and priority to U.S. Provisional Patent Application No. 61/375,732, filed Aug. 20, 2010, the disclosure of which is incorporated herein by reference. The present application is related to the following: US Patent Application Publication Number 20090228057, titled ACCURATE CARDIAC EVENT DETECTION IN AN IMPLANTABLE CARDIAC STIMULUS DEVICE; US Patent Application Publication Number 2009-0259271, US Patent Application Publication Number 2010-0004713, and US Patent Application Publication Number 2010-0094369, each titled METHODS AND DEVICES FOR ACCURATELY CLASSIFYING CARDIAC ACTIVITY; and US Patent Application Publication Number 2011-0098585 and U.S. Provisional Patent Application Ser. No. 61/255,249, each titled METHODS AND DEVICES FOR IDENTIFYING OVERDETECTION OF CARDIAC SIGNALS, the disclosures of which are incorporated herein by reference.

TECHNICAL FIELD

The present invention relates generally to implantable medical device systems that sense and analyze cardiac signals. More particularly, the present invention relates to implantable cardiac devices that capture cardiac signals within an implantee's body in order to classify cardiac activity as indicating or not indicating therapy.

BACKGROUND

Implantable cardiac devices typically sense cardiac electrical signals in an implantee and classify the implantee's cardiac rhythm as indicating therapy or not indicating therapy. A rhythm indicates therapy if it is believed that delivering therapy would provide an improvement to the patient's condition that outweighs discomfort or risk associated with therapy; otherwise, the rhythm does not indicate therapy. For example, ventricular fibrillation almost always indicates therapy, some ventricular tachyarrhythmia indicates therapy, and atrial fibrillation often may not indicate therapy. Clinical judgment as to whether therapy is indicated may vary.

The nomenclature used herein indicates that a signal is sensed by an implantable cardiac device, events are detected in the sensed signal (yielding detected events or detections), and cardiac activity is classified by use of the detected events in a rhythm classification step or process. Rhythm classification is often directed at identifying rhythms such as ventricular fibrillation or certain tachyarrhythmias indicating therapy. Some such systems then make therapy decisions reliant on the classification of the cardiac rhythm. Rhythm classification often includes interval or rate analysis. For example, detected events are separated by intervals, and several intervals can be used to generate an average interval. The detected heart rate can then be calculated using the average interval. Rate is often a primary factor in identifying conditions such as ventricular fibrillation (VF) and/or ventricular tachyarrhythmia.

To accomplish accurate rhythm classification using rate analysis, events should be detected accurately. A cardiac electrogram includes several portions (often referenced as "waves") that, according to well known convention, are labeled with letters including P, Q, R, S, and T, each of which corresponds to particular physiological events. Detection methods are often designed to detect the R-wave or QRS complex, though this is not required. Typically for purposes of ascertaining rate, the aim is to predictably count each cardiac cycle, so any portion of the cardiac cycle, if repeatedly identified, can serve as the focus for detection. Overdetection (such as a double or triple detection) may occur if the device declares more detected events that its design contemplates for a single cardiac cycle. Examples of overdetection (in a system designed for a single detection per cardiac cycle) include the detection of both an R-wave and a trailing T-wave, multiple detections of a wide QRS complex, or early detection of a P-wave followed by detection of a trailing part of the QRS complex or a T-wave from the same cardiac cycle. Overdetection may also occur if noise causes an event to be declared when no cardiac event has taken place, for example, due to external defibrillation, external noise, pacing artifact, skeletal muscle noise, electro-therapy, etc. Even if rate analysis is not used in rhythm classification (for example, signal shape analysis could be used to the exclusion of rate), accurate detection of cardiac events would be useful to improve analytical accuracy.

Overdetection can lead to overcounting of cardiac cycles. For example, if one cardiac cycle takes place and a detection algorithm mis-identifies this one cycle as multiple cardiac cycles, overdetection has occurred. If the heart rate is then calculated by counting true detections as well as overdetections, overcounting occurs. Calculated heart rates may be used alone or in combination with other factors to classify cardiac rhythms. Miscalculation of heart rate can lead to incorrect rhythm classification and therapy decisions. For example, miscalculating heart rate by overcounting can cause elevated rate calculation and, since many implantable devices use rate for identifying conditions indicating therapy, for example ventricular fibrillation, miscalculating heart rate by overcounting can lead to inappropriate therapy. Inappropriate therapy is widely considered undesirable.

New and/or alternative methods and devices for cardiac signal analysis are desired.

SUMMARY

Various illustrative embodiments of the present invention are directed toward improved accuracy in cardiac signal analysis by implantable medical devices. Some illustrative embodiments identify overdetection of cardiac events. In an illustrative example, overdetection is identified using analysis of the apparent width of detected events. Some illustrative embodiments also correct at least some captured data and use the corrected data to make operational decisions. The invention may be embodied in methods and/or devices. Other embodiments identify additional purposes to the identification of overdetection beyond just correcting the rate calculation. Some embodiments provide for combinations of diverse metrics for purposes of identifying overdetection.

DETAILED DESCRIPTION

The following detailed description should be read with reference to the drawings. The drawings, which are not necessarily to scale, depict illustrative embodiments and are not intended to limit the scope of the invention. Some of the following examples and explanations include references to issued patents and pending patent applications. These references are for illustrative purposes and are not intended to limit the present invention to the particular methods or structures from those referenced patents and patent applications. Unless implicitly required or explicitly stated, the methods below do not require any particular order of steps.

Figure 1A:
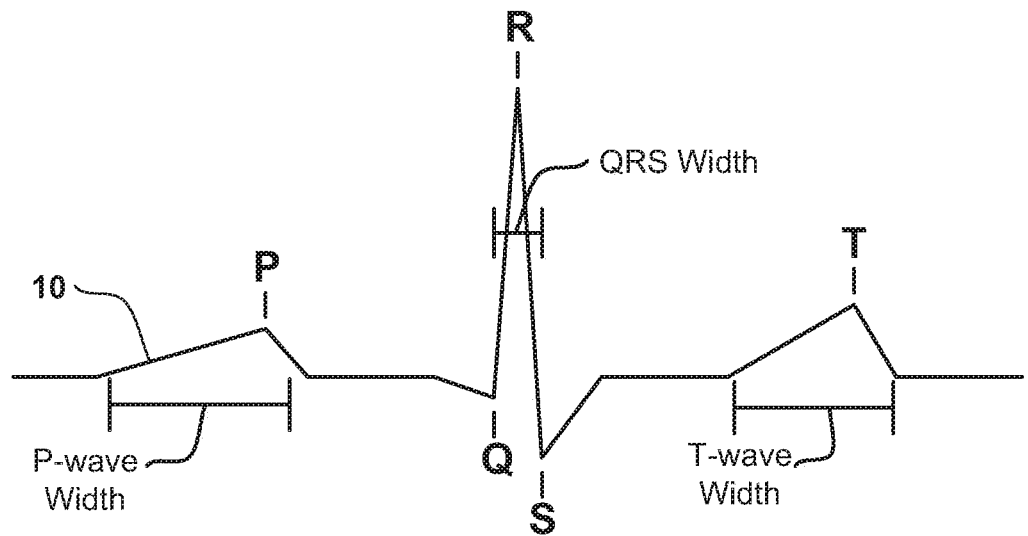
FIG. 1A illustrates a convention for identifying features in a cardiac cycle.

FIG. 1A illustrates a convention for identifying features in a cardiac cycle. A trace is shown at 10 and represents sensed cardiac signals changing with time. The convention marks a P-wave, representing atrial depolarization, followed by the QRS complex, representing ventricular depolarization, followed by the T-wave, representing repolarization of the ventricles. Repolarization of the atria is often masked by other features of the cardiac cycle and may not be visible, as is the case in FIG. 1 A.

Figure 1B:
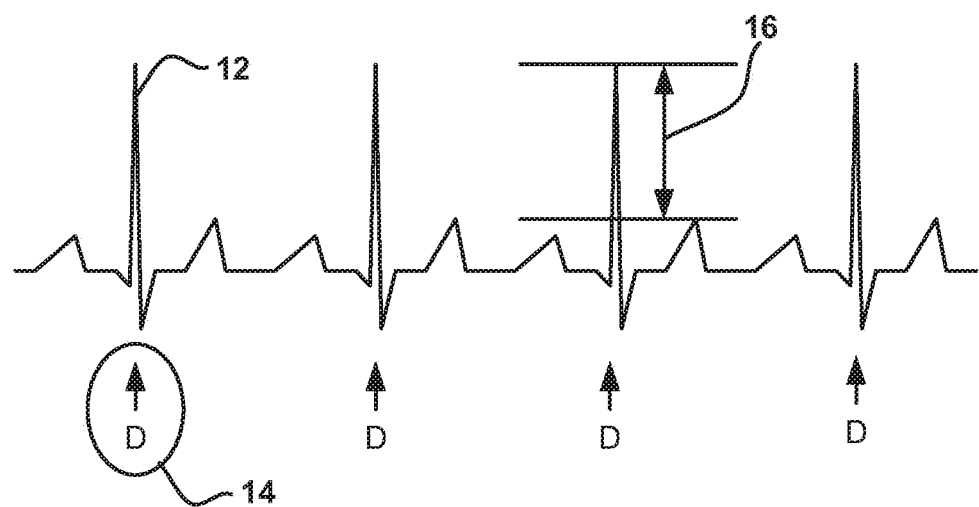
FIG. 1B illustrates normal detection of a cardiac signal.

Depending upon the location of the electrodes used to capture the signal, the QRS complex is often the largest amplitude portion of the cardiac cycle. Implantable cardiac stimulus and/or monitoring systems often use methods to detect solely the R-wave as a way to count cardiac cycles. FIG. 1B illustrates one-to-one detection in a cardiac signal using R-waves for detection of cardiac cycles. The signal in FIG. 1B is shown at 12 and includes a number of cardiac cycles each having prominent R-waves. Detections are indicated by the "D" and arrow underneath the signal, for example as shown at 14. The illustration shows one-to-one detection with each D corresponding to an R-wave peak.

The signal in FIG. 1B is accurately detected on a one-to-one basis, with each cardiac cycle resulting in a single detected event. One reason why FIG. 1B shows accurate sensing is the signal 12 has a large R-wave amplitude to T-wave amplitude ratio. This is shown by the difference between the amplitudes of the R-wave peak and the largest non-R-wave, here, the T-wave, as highlighted at 16.

Figure 2:
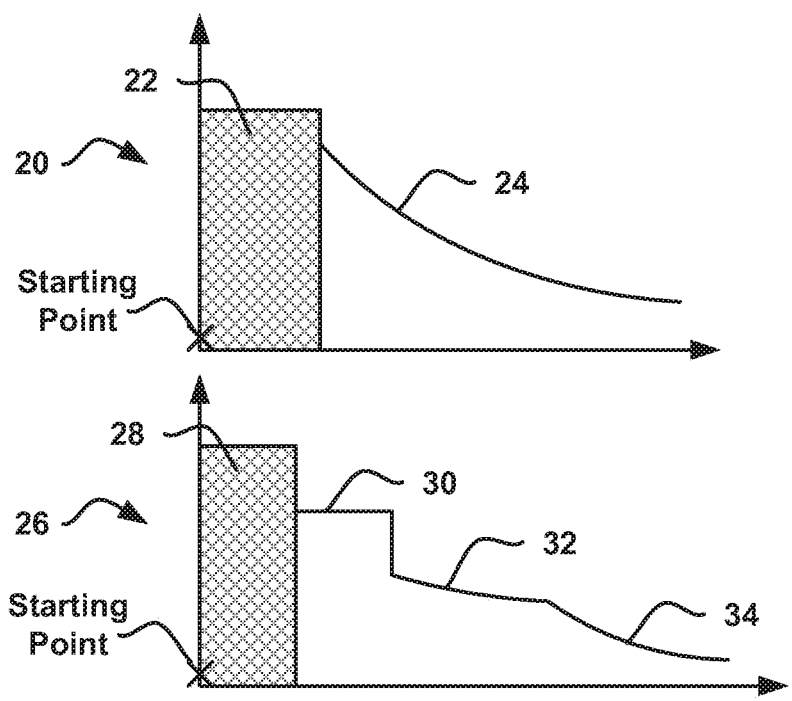
FIG. 2 shows illustrative detection profiles for detecting cardiac events by amplitude measurement.

In many systems, the cardiac electrical signal is monitored and compared to a detection threshold. When the monitored signal exceeds the detection threshold, a detected event is declared. The detection threshold may scale to sensed signal amplitude and may be shaped according to a detection profile. Some illustrative examples are shown in US Patent Application Publication Number 2009-0228057, titled ACCURATE CARDIAC EVENT DETECTION IN AN IMPLANTABLE CARDIAC STIMULUS DEVICE. FIG. 2 shows illustrative detection profile shapes.

Referring to FIG. 2, a first detection profile shape is shown at 20. The detection profile includes two main parts: a refractory period 22, during which new detected events are not declared, and a decaying threshold period 24, during which the sensed signal is compared to a time-decaying threshold and, if/when the sensed signal is of larger amplitude than the time decaying threshold, a new detected event can be declared. In the example, the refractory period 22 is used to prevent immediate redetection of a cardiac cycle during a predetermined period of time, often in the range of 30-350 milliseconds, for example. The time decay 24 may start at a percentage of the average amplitude determined from the peak amplitude of one or more previously detected events, applying the detection profile in proportion to the amplitude of cardiac signal peaks, which can change for a number of reasons.

A more complex detection profile is shown at 26, this time including a refractory period 28 followed by several detection periods 30, 32, 34, with different threshold amplitudes and durations for each detection period 30, 32, 34. The threshold in detection periods 30, 32, 34 may decay or may be constant, depending upon preferences, and may be tailored to avoid overdetecting certain artifacts such as the T-wave, while still allowing the detection profile to track to lower amplitudes as time passes. The eventual decay to lower amplitudes can help to avoid underdetection if the cardiac signal of the patient diminishes in amplitude, for example due to onset of a tachyarrhythmia. In some examples, one or more of periods 30, 32, 34 may increase in amplitude, for example to accommodate known or predicted artifacts, if desired.

With each detection profile 20, 26, when the sensed signal amplitude exceeds the detection threshold defined by the profile 20, 26 outside of refractory 22, 28, a new detected event is declared, and the detection profile is reset to its starting point. The refractory period 22, 28 follows, with the detection period 24 or 30, 32, 34 after that. Some embodiments can switch from one detection profile to another in response to detected conditions, for example selecting from among the profiles 20, 26 (or other profiles) depending on rate, morphology match or mismatch, absolute or relative amplitude of signal or noise, signal-to-noise ratio or other factor(s).

Figure 3A:
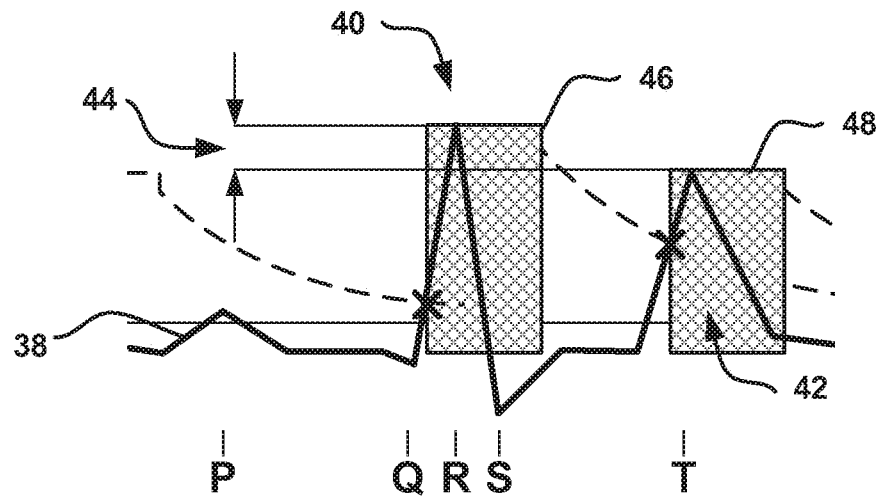
FIG. 3A shows an example cardiac signal being overdetected.
Figure 3B:
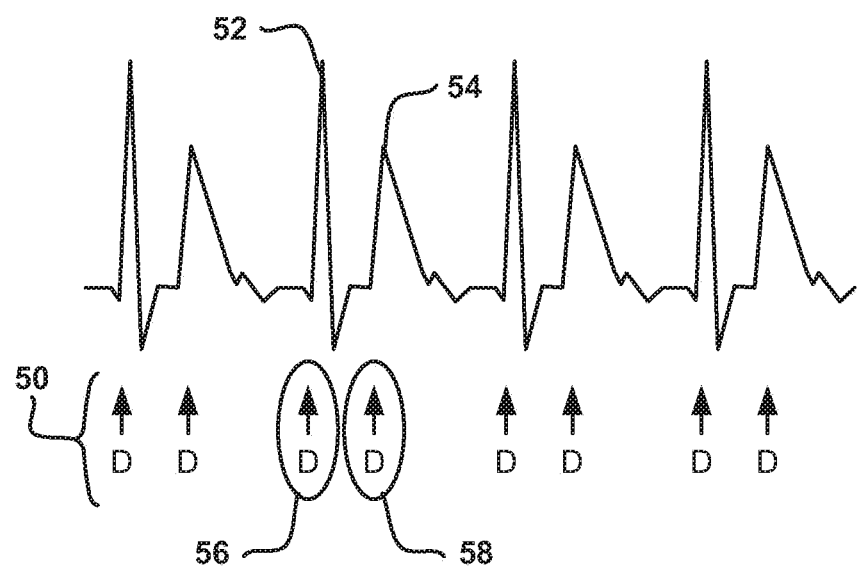
FIG. 3B illustrates consistent overdetection of the cardiac signal of FIG. 3A.

The profiles 20, 26 take advantage of amplitude variation between components of the cardiac signal. When the R-wave (or any other repeatable component of each cardiac cycle) stands out clearly against the rest of the signal, detection can be highly accurate. However, the cardiac signal morphology of patients can vary widely due, for example, to physiological, nutritional, pharmaceutical, therapeutic and/or disease-related conditions. When the R-wave is not as prominent as shown in FIGS. 1A-1B, even sophisticated systems may encounter difficulties obtaining one-to-one detection and accurate rate calculation. FIGS. 3A-3B illustrate a manner in which a cardiac signal can be overdetected.

In FIG. 3A, a single cardiac cycle is shown with the signal trace at 38 having P, Q, R, S and T features identified. In the signal trace 38, the T-wave 42 is large relative to the R-wave 40, as shown at 44. This can make overdetection possible, depending upon features of the detection methodology. In the example, an illustrative detection profile is shown 46. The detection profile 46 shows a refractory period starting at detection of the QRS complex, followed by a decay period. The decay period uses a percentage of the amplitude of the R-wave 40 as a starting point for the decay. The detection profile 46 and signal trace 38 meet due to the T-wave 42, causing another detected event which, in this instance, is an overdetection. A new detection profile 48 is then applied, using a percentage of the amplitude of T-wave 42 as a starting point for its decay. Two detected events occur within a single cardiac cycle, illustrating one type of overdetection.

The design intent in this illustrative example (and in most of the examples shown herein) is to detect one event for each cardiac cycle. Some systems may instead sense two events (or more) per cardiac cycle, such as a system detecting a ventricular event and an atrial event. Overdetection can include detection of more events per cardiac cycle than is intended. For example, dual chamber sensing systems may rely on detecting a ventricular event and an atrial event with each cardiac cycle; overdetection for such systems can include detecting an event in either chamber (or events in each chamber) beyond those which are intended. Such overdetection can impair accuracy of analysis of the patient's cardiac state.

FIG. 3B illustrates repeated overdetection of the nature shown in FIG. 3A. Markers from a detection system are shown at 50, with each "D" representing a new detected event. Those skilled in the art will recognize that each cardiac cycle is paired with two detected events. For example, for an R-wave at 52 and the following T-wave at 54, there are two detections at 56 and 58, even though R-wave 52 and T-wave 54 are both within a single cardiac cycle. If all of the detections 50 are counted as each representing a separate cardiac cycle, the system will estimate a cardiac rate that is double the actual rate. If signal shape analysis (such as template correlation) is used, the inclusion of two different morphology-types (R-wave and T-wave) in the set of detections may cause poor or widely variable analysis outcomes, possibly suggesting polymorphic arrhythmia and indicating therapy. If rate is used, overcounting can lead the system to incorrectly calculate a high cardiac rate and conclude that a tachyarrhythmia is occurring, potentially indicating therapy.

Figure 4:
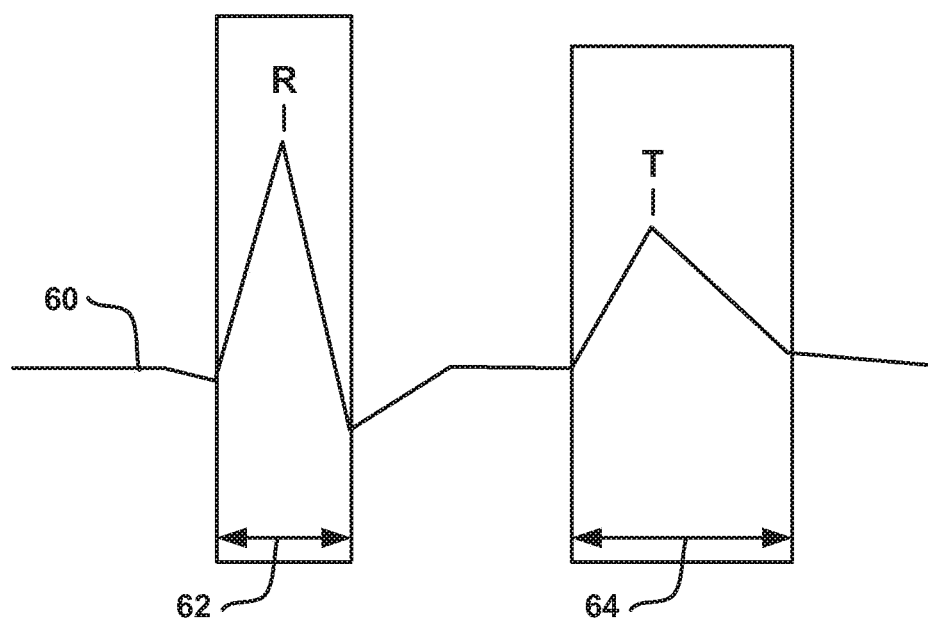
FIG. 4 shows the widths of two features of a typical cardiac cycle.

FIG. 4 compares the width of two features of a typical cardiac cycle. A cardiac signal trace is shown at 60, and an R-wave and a T-wave are marked. The R-wave has a width as shown at 62; width 62 can be referred to as the R-wave width or the QRS width. The T-wave has a width as shown at 64. For many patients and/or system configurations, the T-wave will be wider than the R-wave. However, for some patients and/or for some sensing "views" of the heart, the R-wave can be wider than the T-wave.

Figure 5:
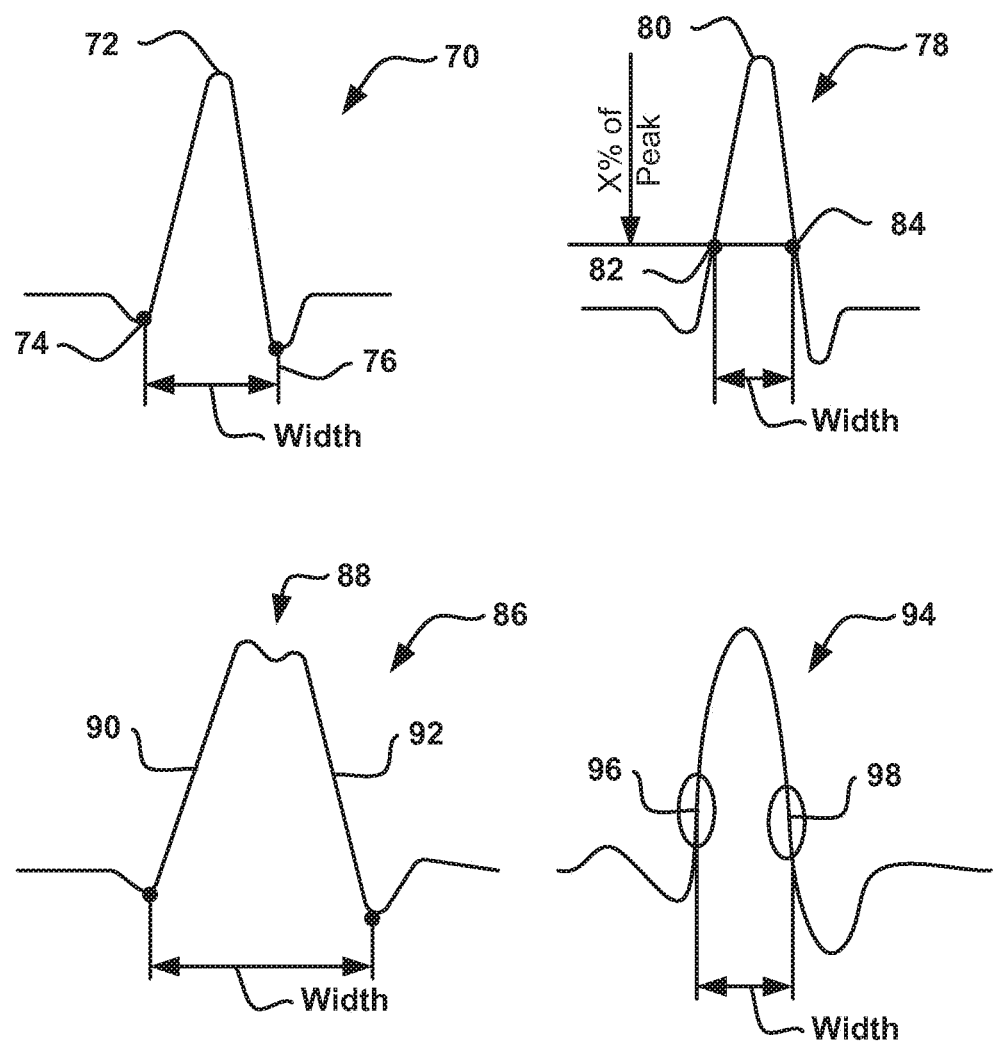
FIG. 5 shows illustrative methods of measuring cardiac event width.

There are several ways to define the "width" of a detected event, as shown in FIG. 5. For example, as shown at 70, width can be calculated for a detected event 72 from a first-derivative zero or "turning point" 74 that precedes the detected event peak 72 to a turning point 76 that follows the detected event peak 72. In another example, as shown at 78, the peak amplitude of a detected event 80 can be used to identify "down points" at a predetermined percentage of the peak 80 (for example, 20%; other percentages can be used). When the signal crosses the down point threshold, down points 82 (before the peak 80) and 84 (after the peak 80) are defined, and the duration of time between points 82 and 84 is measured and used as the "width". The down threshold may also be the baseline or zero for the signal or it may be calculated using a percentage of the difference between the positive and negative peaks for the signal.

Another example calculation of width is shown at 86. Here, for illustrative purposes, a notched peak 88 is shown. Notched peaks 88 are known to occur but will not always be present. Width measurement can be tailored to accommodate notched peaks. The illustrative calculation can be performed for a single peak as well. In the example, the longest monotonic segments on either side of the peak 88 are identified, as shown at 90, 92. A monotonic segment may be defined as a segment having no turning points—a "single slope" segment. In this example, width is defined from the start of the longest monotonic segment 90 that precedes the peak 88, to the end of the longest monotonic segment 92 that follows the peak 88, within the window of data shown.

Another illustrative width calculation is shown at 94. In the example at 94, second derivative zero points are identified in the signal, and these points preceding 96 and following 98 the signal peak are highlighted. The second derivative zeros 96, 98 are also referred to as inflection points of the signal. The duration between the second derivative zeros 96, 98 can be calculated and treated as the width of the signal.

Any of the illustrative width measurements 70, 78, 86, 94 may be used to estimate the width of detected events.

Figure 6:
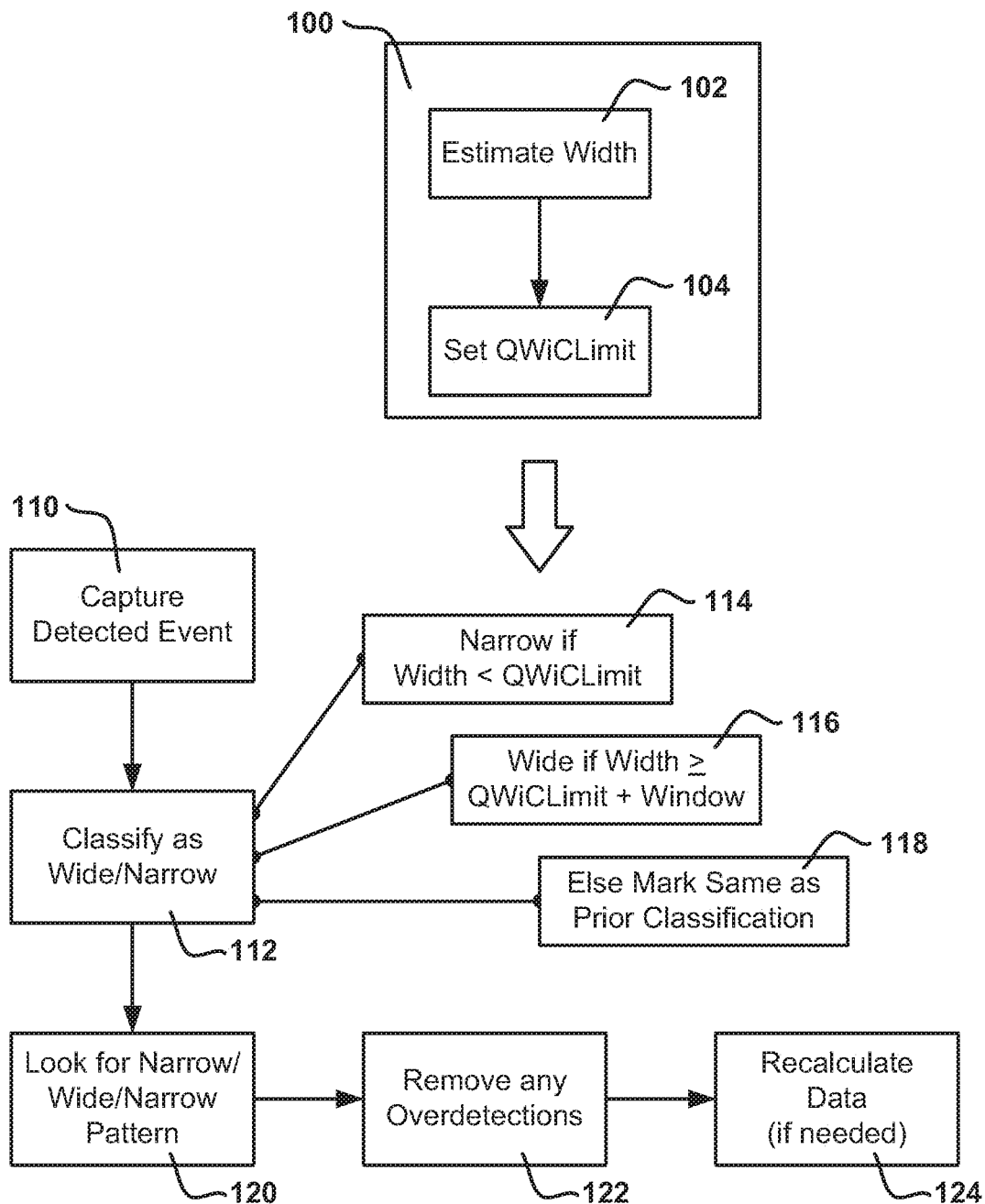
FIG. 6 illustrates in block form a method of identifying overdetection of a cardiac signal using analysis of detected event width.

FIG. 6 illustrates a method of identifying overdetection of a cardiac cycle using detected event width analysis. A first part of the method sets a QRS Width Count Limit (QWiCLimit), as shown at 100. An estimated width of the QRS of the signal is calculated, as shown at 102, and QWiCLimit is set using the estimated width, as shown at 104. The width can be estimated using any suitable manner, including, for example, the methods shown in FIG. 5. In illustrative examples, the estimated width can be calculated as an average width of a number of detected events, as a median of several measurements, as the width of a static or dynamic template, or as some combination of such factors. For example, the estimated width may be calculated as one half of a width of a static template plus one half of a median width from a previous 10 detected events.

The QWiCLimit can be set by adding a buffer to the estimated width. In one example, QWiCLimit is 1.25 times the estimated width. In another example, QWiCLimit equals the estimated width plus a time duration, for example, 25 milliseconds. In another example, QWiCLimit is calculated as an average width plus two standard deviations of the average width, using known statistical formulations. QWiCLimit may be set using a buffer that is indexed to cardiac rate, for example with the buffer being 25 milliseconds at rates below 90 bpm, 20 milliseconds for rates from 90 bpm to 140 bpm, and 15 milliseconds for rates above 140 bpm, for example. Other index variables and rate boundaries may be set, instead. A minimum or maximum QWiCLimit can be set, if desired.

QWiCLimit is used in the illustrative example for identifying overdetected events. As shown at 110, the method includes capturing a detected event, which is then classified as Wide or Narrow, as shown at 112. Three rules for classifying the detected event as wide or narrow are shown at 114, 116, 118. If the Width is less than the QWiCLimit, the detected event is classified as narrow, as shown at 114. If the Width is greater than QWiCLimit plus a Window variable, then the detected event is classified as wide, as shown at 116. The "Window" variable may be relative or fixed. In one example, Window is set to about 40 milliseconds, while in other illustrative examples, Window is set at 10-35% of the QWiCLimit, set to one or two standard deviations of the average width calculation, set to other fixed values (15-60 milliseconds) or set using a rate-based index, for example 5-25% of the inverse of estimated cardiac rate. Finally, if the width does not meet either of 114 or 116, then the newest detected event is classified to be the same as the previous detected event, as shown at 118.

Next, the method observes whether a narrow-wide-narrow pattern suggesting overdetection has occurred, as shown at 120. If a pattern suggesting overdetection is found at 120, the method removes any identified overdetections from analysis of rate, as shown at 122. Next, data is recalculated, if needed, as shown at 124. With steps 122 and 124, if overdetection is found, data that results from overdetection is removed from the analysis and calculations based on overdetections are corrected. The narrow-wide-narrow pattern is one illustrative example of an over-detection type pattern that may be sought at step 120; other useful patterns may apply.

Figure 7:
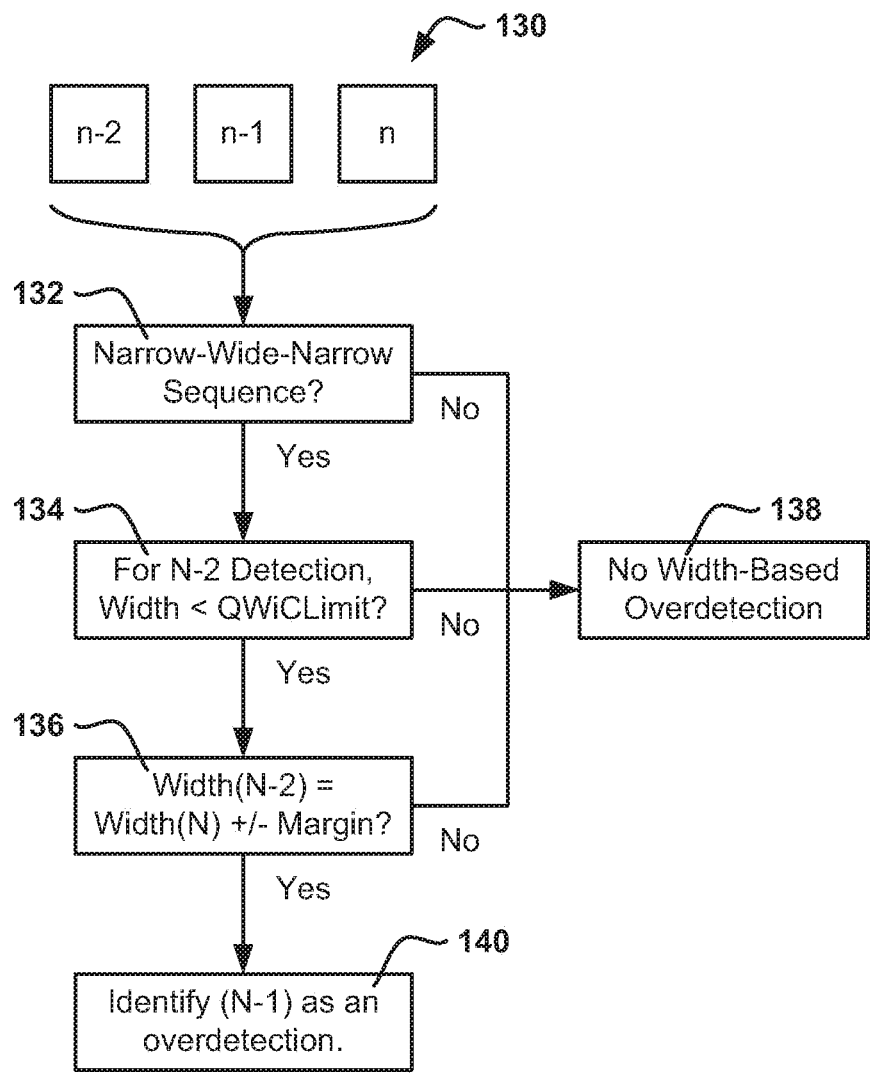
FIG. 7 shows another illustration of a method for identifying overdetection using analysis of detected event width.

An illustrative pattern analysis for use in block 120 is illustrated in FIG. 7. The method analyzes three detected events numbered n, n–1 and n–2, as shown at 130, where n is the most recent of the three events and n–2 is the oldest of the three. The method includes observing whether a narrow-wide-narrow sequence has occurred, as noted at 132. If so, the method next determines whether the n–2 detection has a width less than QWiCLimit, as shown at 134. The check at block 134 ensures that the oldest of the detected events, n–2 was not marked as narrow simply because it had a width within the "window" and was marked the same as a prior event at block 118 in FIG. 6. This check at 134 may be omitted in some embodiments.

The method also determines whether the n–2 width is within a predetermined Margin of the width of event n, as shown at 136. This optional step ensures that n and n–2 are relatively similar in width. In an illustrative example, the Margin is set to about 20 milliseconds. Other fixed or relative values may be used for Margin. As an alternative to the check at 136, the method may ensure that n and n–2 are similar to one another using a correlation analysis by comparing the events to one another. In yet another alternative, each of event n and event n–2 can be compared to a "normal" template and, if both n and n–2 correlate well, the method can proceed to block 140. In another example, step 136 may be omitted.

Figure 8:
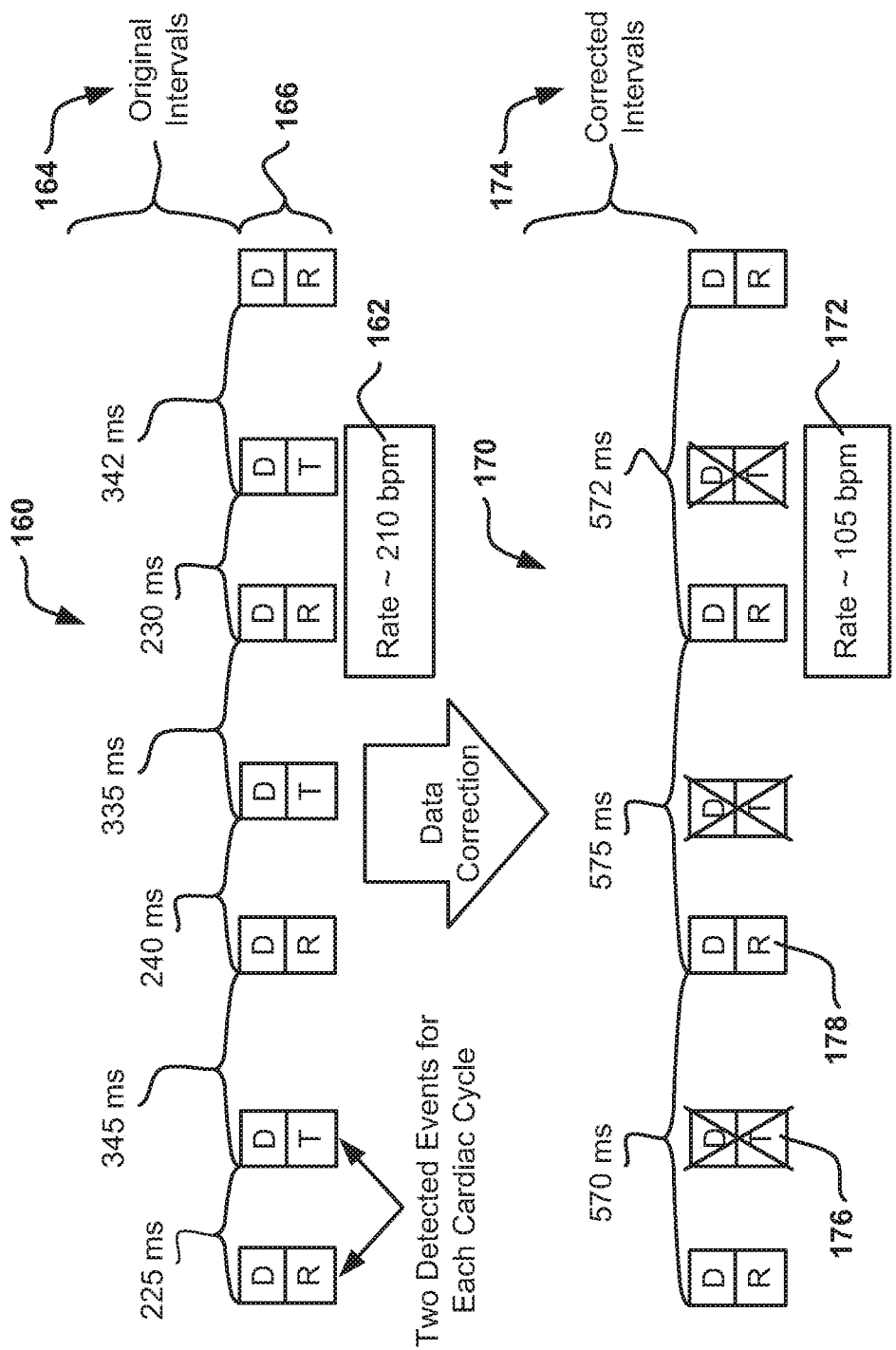
FIG. 8 illustrates a method of correcting overdetected data.

In this example, if any of conditions 132, 134 and 136 fail, no Width-based overdetection is found, as indicated at 138. If all three conditions 132, 134 and 136 are met, then the n–1 event is identified as an overdetected event, as indicated at 140. FIG. 8 illustrates the analysis that follows an identification of overdetected event(s).

The example in FIG. 8 begins with an initial calculation shown generally at 160. As shown at 162, a rate of 210 beats-per-minute (bpm) is calculated using the set of original intervals 164. The original intervals occur between detected events (D) which are characterized as either R or T wave detections, as shown at 166. As indicated, due to overdetection, there are two detections for each cardiac cycle.

Identification of overdetection, in this example, leads to the data being corrected as shown at 170. A corrected beat rate of 105 bpm is calculated as shown at 172 from corrected intervals 174. The intervals are corrected by removing the T-wave detections 176 and leaving the R-wave detections 178, and recalculating the intervals as if no T-wave detections 176 occurred. In an alternative embodiment, the R-wave detections 178 could be marked as the overdetections, with intervals recalculated between the T-wave detections 176 to yield a similar result.

FIG. 8 illustrates a method of modifying detected event data to correct for overdetection and/or to reduce the impact of overdetection. In another embodiment, the impact of overdetection can be reduced by ignoring the overdetected data completely, for example, if an event is overdetected, then both intervals on either side of the event may be ignored for rate estimation. In another example, if both rate and morphology analysis are available, identification of overdetected events may trigger reliance on morphology analysis only. For example, the accurate detections may be compared to a stored normal sinus template to observe high correlation and determine no arrhythmia is occurring or, alternatively, to observe low correlation to a normal signal template and determine an arrhythmia appears likely. In another example, stored templates may themselves be templates of treatable or abnormal rhythms, if such templates are formed for a patient. In another example, after overdetection is identified, a set of data may be discarded until overdetection no longer occurs. In another example, if multiple sense vectors are available on different sense channels, overdetection of one channel may cause the system to ignore the overdetected channel and use other channel(s), as available, to monitor cardiac activity.

Figure 9:
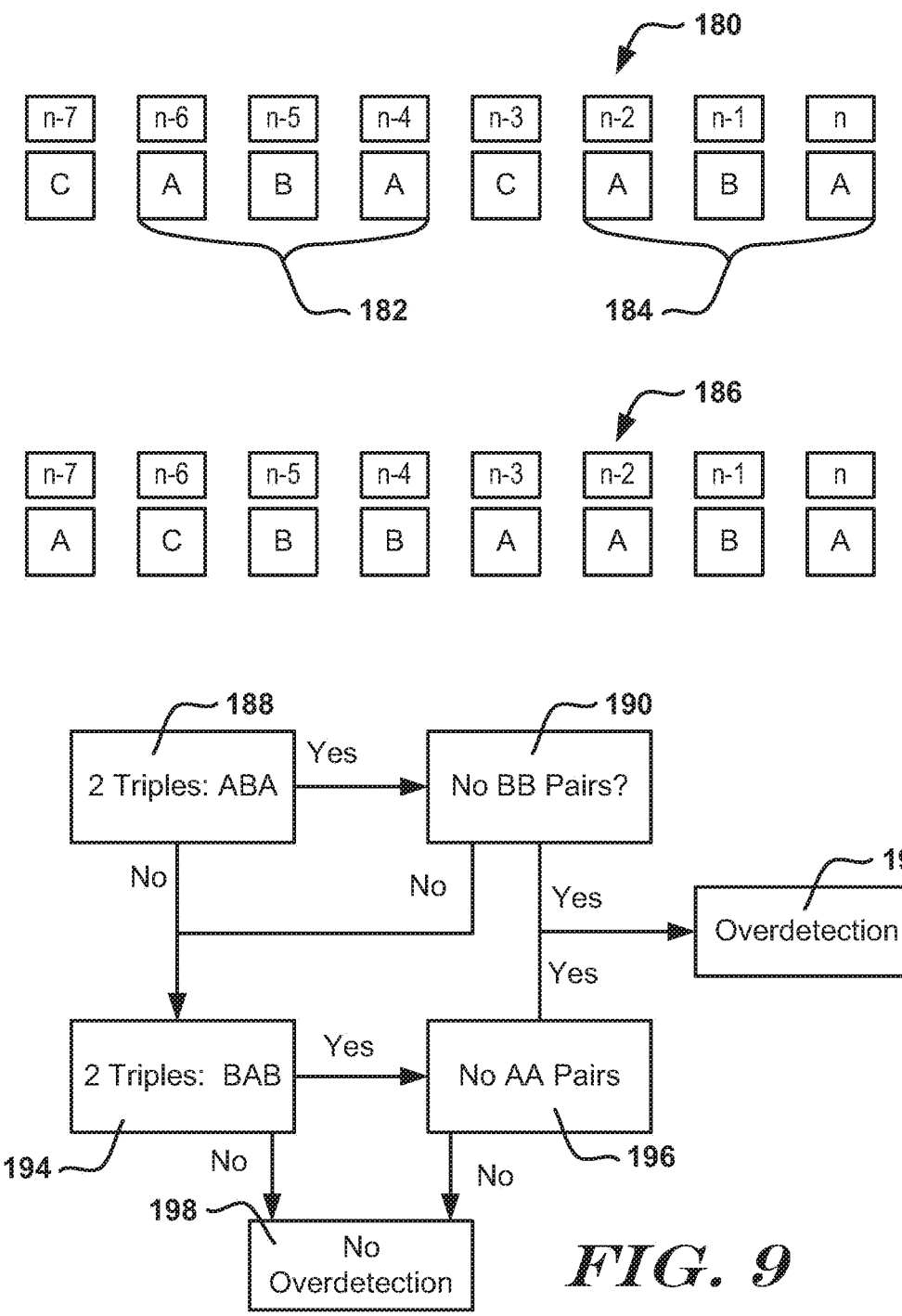
FIG. 9 illustrates another method of data analysis for identifying overdetection through analysis of a larger set of detected events.

FIG. 9 shows overdetection analysis covering a set of detected events. Rather than reference to a set of 3 events, as shown by FIG. 7, above, FIG. 9 covers a larger set of data and looks for patterns that suggest overdetection. For example, a set of eight events is shown at 180 and contains two triplets, shown at 182, 184, that may suggest overdetection.

Each triplet 182, 184 takes the form of "A, B, A," where A is one category of event and B is a counter to A. For example, if A indicates a narrow cardiac event, then B indicates a wide cardiac event. When multiple ABA triplets occur in the set of eight events 180, then overdetection is identified and at least one of the "B" events is identified as an overdetection.

In this example, if multiple qualifying "triplets" do not occur, as shown in the set of events at 186, then overdetection may not be identified. In the set of events shown at 186, events marked with a C do not meet criteria for either A or B and instead fall "in-between." For example, if A represents narrow cardiac events and B represents wide cardiac events, then C would represent cardiac events that fall between thresholds for wide and narrow.

An illustrative system could mark events that are less than 80 milliseconds wide as narrow, and events greater than 120 milliseconds as wide, with the range from 80-120 milliseconds being a band in which events are considered neither wide nor narrow. Continuing the example, events that are less than 80 milliseconds wide could be "A" events, events that are more than 120 milliseconds wide could be "B" events, and events that are in the range of 80-120 milliseconds wide are marked as "C" events. Events may also be marked using the method of FIG. 6, above, for example, with the modification that events would be marked as "A" if they are narrow as in block 114, "B" if they are wide as in block 116, and "C" otherwise (rather than as wide or narrow per block 118).

In the example shown, a series of rules are applied to determine whether overdetection is identified. As shown at 188, two ABA triples are sought in the set of events. If two ABA triples are found, then the method determines whether there are any pairs of BB events, in which consecutive events are of type "B", as shown at 190. If not, then overdetection 192 is found, and a "B" event in at least one of the ABA triples is marked as an overdetection leading to correction of associated data using a method as shown in FIG. 8.

If conditions 188 or 190 fail, the method looks for the converse: two BAB triples, as shown at 194. If there are at least two BAB triples in the set of events, the method next checks where there are any pairs of AA detections, as shown at 196. If no AA pairs occur, then overdetection 192 is found, and an A event in at least one of the BAB triples is marked as an overdetection leading to correction of associated data using a method as shown in FIG. 8. If at least one AA pair occurs, or if there are less than two BAB triples in the set of events, the method finds no overdetection, as shown at 198. For example, assuming a width analysis is used, the ABA triple may be narrow-wide-narrow, while the BAB triple may be wide-narrow-wide. In the example of FIG. 9, each of these triples is considered an indication of likely overdetection. In other examples, only one triple is considered to indicate likely overdetection, while the other may be suggestive of arrhythmia.

The exclusions for BB and AA pairs, shown at 190, 196, provide a way to avoid counting overdetection in response to random detection. The purpose, in part, is to identify characteristics of the detected events that may indicate overdetection. The rule is provided because, in some examples, consecutive detection of the sort "BB" suggests that an "ABA" triplet is not a result of overdetection. For other examples, these exclusions 190, 196 may be omitted and replaced with other factors, such as coupling characteristics or a majority rule.

In another example, a coupling characteristic rule looks at the intervals of a triplet, for example, an "ABA" triplet more likely suggests overdetection if at least one of the "A-B" or "B-A" intervals is shorter than one of a fixed threshold or a relative threshold and/or if the A-B interval is markedly different from the B-A interval. Further examples may look to other second tiers of analysis, such as requiring that one or both of the "A" detections in the "ABA" triplet correlate to a template, or that the "A" detections correlate well to one another. In another example, the method may call for "B" of the "ABA" triplet to correlate poorly or be uncorrelated to a template or to at least one of the "A" detections. In these examples, the roles of "A" and "B" may be reversed when contemplating, for example a "BAB" triplet.

In another example, a majority rule would find that an "ABA" triplet does not suggest "B" is an overdetection if more than half of the recent detections are of the "B" type. Thus a sequence of B-A-B-A-B-A-B-B may suggest the "A" is the overdetection rather than the "B".

In the example shown in FIG. 9 other characteristics could be used in place of or in addition to width. For example, high correlation to a static or dynamic template could be used. If a template is used, then high correlation could be the "A" markers and low correlation could be the "B" markers, while C markers would be for events that fall in-between "high" and "low" boundaries (if such a gap is provided). In another example, the "A" markers stand for low correlation and the "B" markers stand for high correlation. It should be noted that in this example, the high and low correlation can be used to improve detection accuracy to avoid overcounting, rather than the more common use of correlation to directly identify malignant or benign heartbeats. Templates may be static (stored representative signals) or dynamic (changing representative signals such as a recent captured signal, an average of several recent captured signals, etc.), and may represent "normal" captured signals or may represent select "abnormal" captured signals such as a bundle-branch block signal or a particular arrhythmia type.

Figure 13:
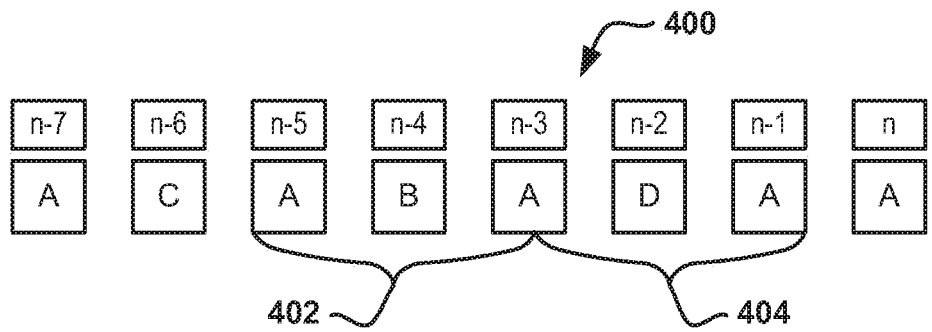
Figure 13:
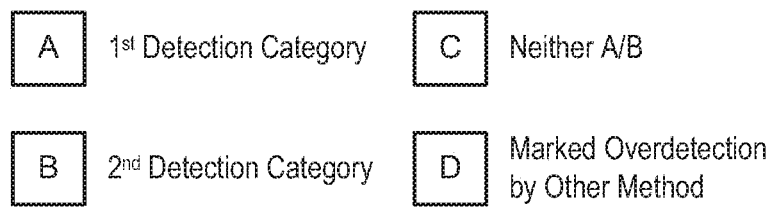
Figure 13:
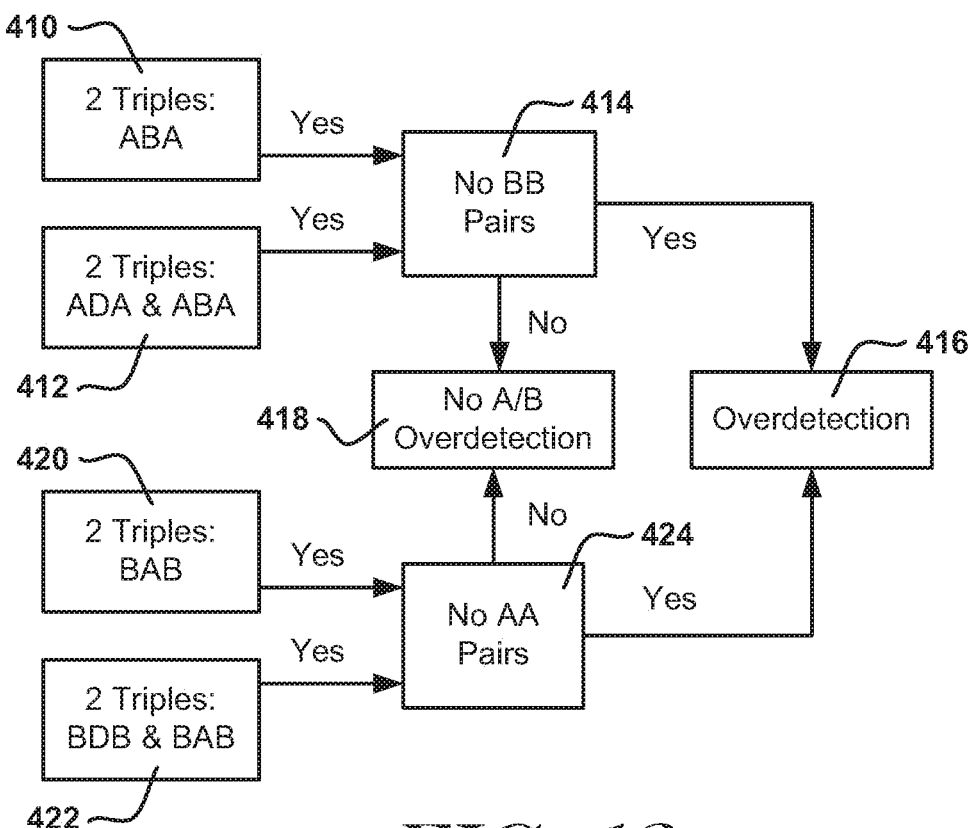

It should be understood that finding "no overdetection" 198 does not mean that other methods of overdetection identification cannot be used. Instead, it merely indicates that this particular method has not identified an overdetection. FIG. 13, below, shows a further method of integrating multiple overdetection identification methods.

Figure 10:
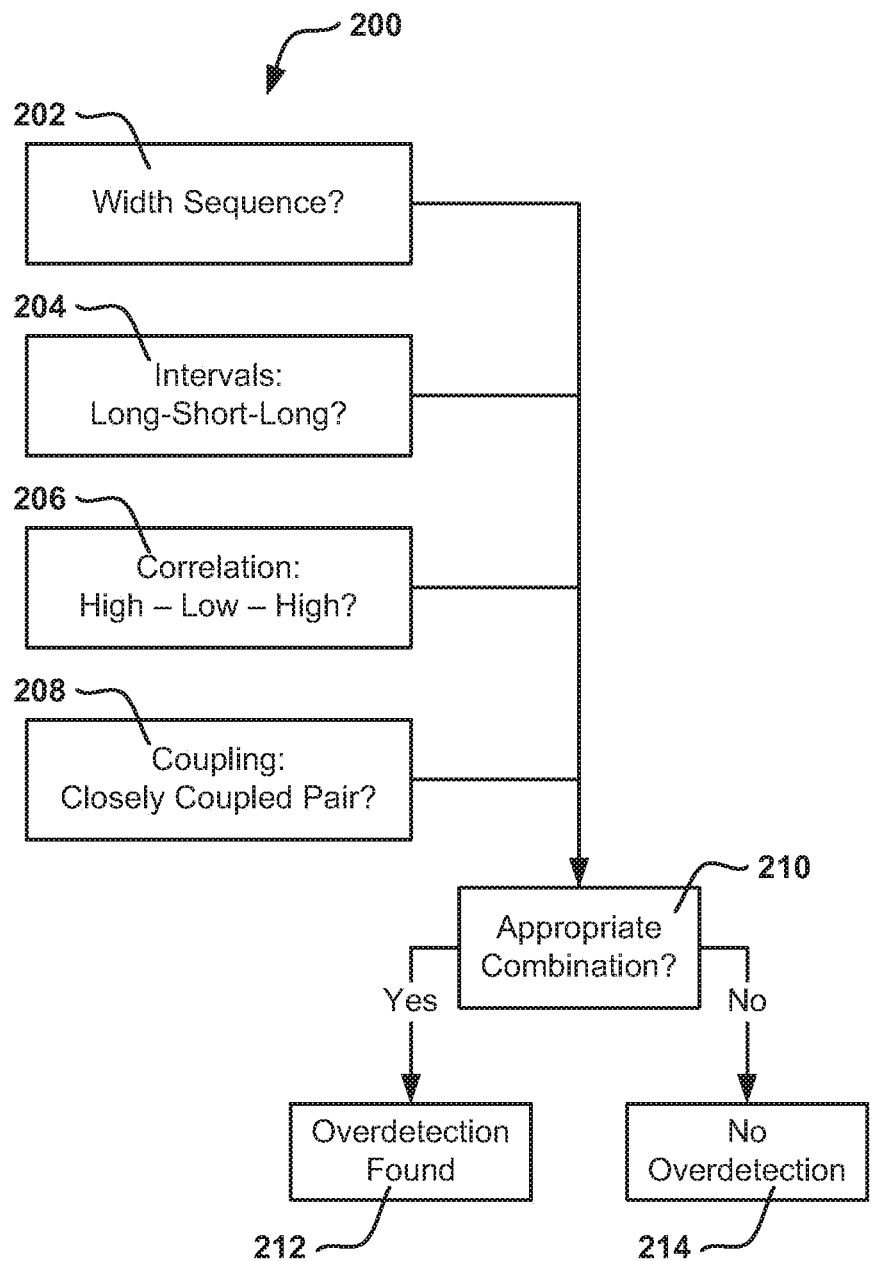
FIG. 10 illustrates another example of identifying overdetection using a number of identifiable traits of a sequence of cardiac events.

FIG. 10 illustrates another example of identifying overdetection using a number of identifiable traits of a sequence of cardiac events. Selected combinations of these traits are used to identify overdetection. As generally shown at 200, there are four identified traits:

As shown at 202, the trait of event width is analyzed in the example to determine whether a
sequence of events shows narrow-wide-narrow combination (or other pattern); As shown at 204, the trait of interval sequence is analyzed in the example to determine whether
a sequence of events shows Long-Short-Long intervals;
As shown at 206, the trait of template correlation is analyzed in the example to determine whether a sequence of events shows High-Low-High correlation (or other pattern); As shown at 208, the trait of close coupling is analyzed in the example to determine whether unusually close coupling of events combined with specific shape characteristics are observed.

If one or more predetermined combinations of traits 202, 204, 206, 208 appear, as shown at 210, then overdetection is found as shown at 212. Each of the sequences noted for 202, 204, 206 may be reversed, for example, to look for Low-High-Low correlation at 206 where the correlation template corresponds to a part of the cardiac cycle that is not supposed to be detected.

In this illustration, the following are examples of combinations that use patterns from multiple characteristics:
In one example, any combination of two of traits 202, 204, 206, 208, if appearing at the same time, leads to a conclusion that overdetection is found 212;
In another example, only certain pairings can result in concluding that overdetection is found, for example, if at least one of 202 or 206 appears in combination with at least one of 204 or 208; or In yet another example, condition 206 can stand alone to identify overdetection, and any pair of the other traits 202, 204, 208 can be used to identify overdetection.

If no appropriate combination appears at 210, then no overdetection is found, as shown at 214. In another embodiment, block 210 does not require a combination and instead determines whether any one of the traits 202, 204, 206, 208 can be identified and, if so, then overdetection is found 212. If overdetection is found at 212, then data correction and any other processes triggered by the identification of overdetection can be performed.

With regard to the interval sequence trait shown at 204, definitions for long and short may be relative, for example, asking whether the "long" intervals are at least 50-150 milliseconds longer than the "short" interval, or absolute, for example asking whether the "long" intervals are more than 500 milliseconds long while the short interval is no more than 250 milliseconds long. In another example, the Long- Short-Long sequence is applied over a larger number of events, for example, 6-10 events may be analyzed. In one example, if at least 7 short-long or long-short pairs appear in a set of 10 events and the last three events form a long-short-long sequence, overdetection is identified. An illustrative approach to defining Long and Short intervals, and to identifying a long-short-long sequence, is shown in US Patent Application Publication No. 2009-0259271, the disclosure of which is incorporated herein by reference.

With regard to template correlation as shown at 206, an example may include using a correlation analysis (such as correlation waveform analysis or difference of area analysis) and characterizing as "High" correlation to a template of greater than 50%, and characterizing as "Low" correlation of less than 25%. Other types of correlation analysis and thresholds for high and low can be defined in other examples. Again an illustrative example is shown in US Patent Application Publication No. 20090259271, the disclosure of which is incorporated herein by reference.

With regard to close coupling as shown at 208, in one example, coupling of two detections within a period calculated as the sum of a Refractory period plus 20-100 milliseconds is contemplated as "close coupling." In a further example, detected event shape is also analyzed by looking for peaks in refractory periods of consecutive detected events that fall within a period in the range of 30-150 milliseconds. For example, given a first event and a second event, if the last peak in the first event's refractory period is within 60 milliseconds of the first peak of the second event's refractory period, along with close coupling of the first and second events, then double detection is identified. An illustrative example of such analysis can be found in the Wide-Complex analysis shown in US Patent Application Publication No. 2009-0259271, the disclosure of which is incorporated herein by reference.

The numeric examples provided for these traits 202, 204, 206, 208 in FIG. 10 are merely illustrative and other ranges, both relative and absolute, may be used instead. As noted in the preceding paragraphs, several examples of individual methods for blocks 204, 206 and 208 are shown in US Patent Application Publication No. 2009-0259271. The present application includes the analysis of block 202 as well as further examples of combining multiple methods of analysis for overdetection.

Figure 11:
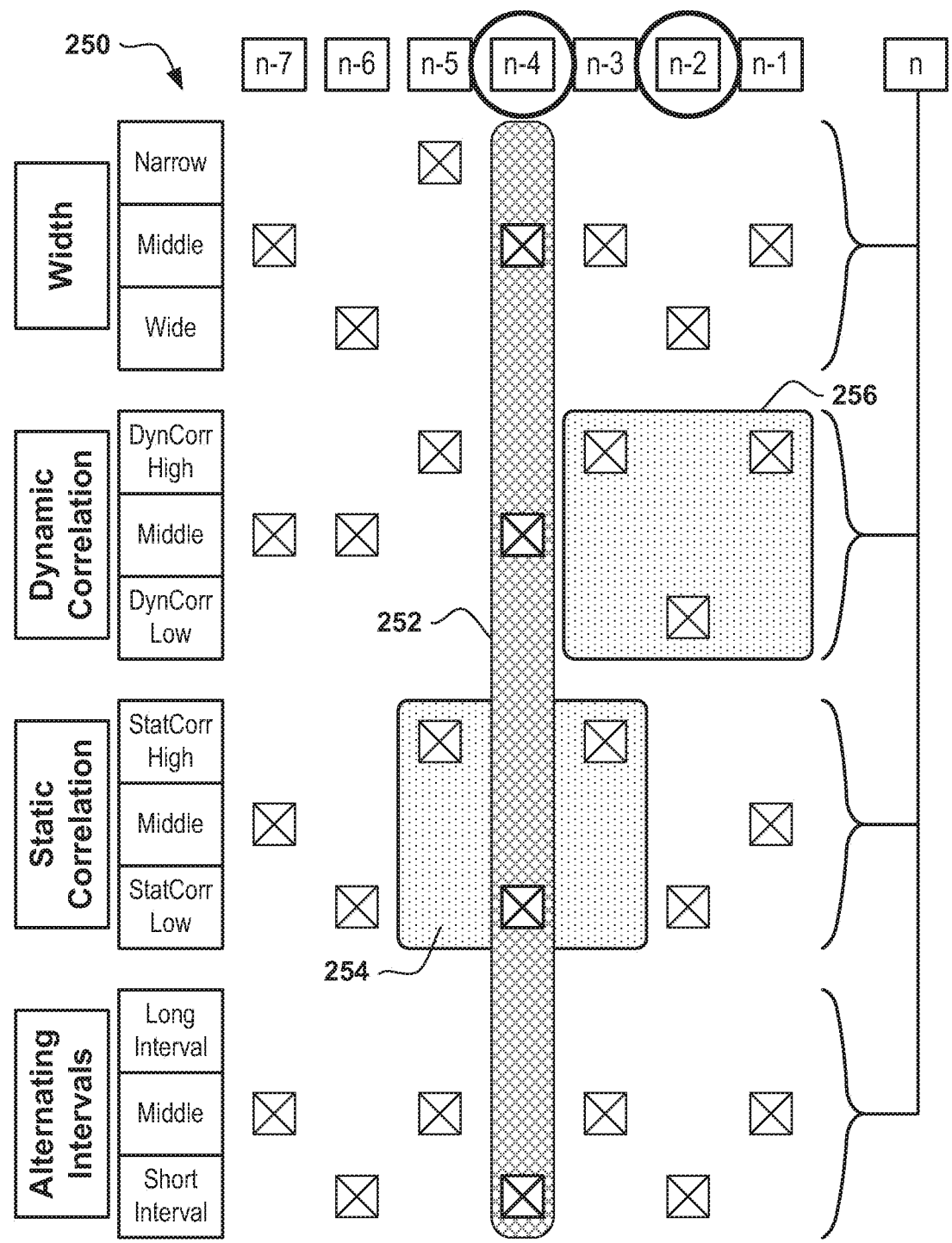
FIGS. 11-13 illustrate analysis methods for identifying overdetection using multiple analytic tools on a set of detected events.

FIG. 11 illustrates integrated analysis of various characteristics of a set of detections for overdetection. A set of detections is shown at 250, with [n] being a most recent detected event in the analysis set 250 and n-7 being the oldest detected event. Categorical analysis of each characteristic is applied:
  Width (Narrow, Middle or Wide)
  Dynamic Correlation (High, Middle or Low)
  Static Correlation (High,
  Middle or Low) Intervals
  (Short, Middle or Long)

For each characteristic, the categories use a high threshold and a low threshold, with a band between the thresholds creating the "middle" categories. Statistical, dynamic and/or fixed boundaries can be used for each of the high and low thresholds for each characteristic. For one or more of the characteristics (or other characteristics, if used), the middle category may be omitted, to yield a more "binary" classification scheme.

In the example of FIG. 13:
  Width indicates the width of a detected event using any suitable "width" measurement; Dynamic Correlation means correlation to a template formed of one of a recent detected event, an average of several recent detected events, or a statistical "median" event, for example, which can change over time with changes in the patient's cardiac electrical signal; Static Correlation means correlation to a stored template indicative of a cardiac cycle of a preselected type, such as a normal signal or an abnormal signal of a particular nature; and Intervals represent one of the duration elapsed between detection threshold crossings or the duration elapsed between an identified amplitude peak associated with a detection threshold crossing.

Other characteristics and categories can be used.

In the illustrative example, each detection is categorized for each of the characteristics. For example, the [n−4] detection, highlighted at 252, has a middle width, middle dynamic correlation, low static correlation, and a short interval. As highlighted at 254, the combination of [n−3], [n−4] and [n−5] detections, when looking only at the static correlation, yields a High-Low-High sequence. By itself, such a sequence may suggest that overdetection has occurred, leading to marking of the [n−4] detected event as an overdetection. However, one of the difficulties with reliance on a single factor such as static correlation is that the underlying thresholds for overdetection are subject to drift and/or error; for example, the static correlation analysis uses a template that can become outdated. Additionally, interval analysis thresholds can become closely spaced at high intrinsic rates, and width analysis can be difficult with patient having wide QRS complexes due to disease process. Those skilled in the art will recognize that any one factor can be prone to difficulty. Greater confidence may be gained by observing additional factors and combinations of factors. Confidence in the result can rise when the two different characteristics have less overlapping data. For example, amplitude of consecutive detected events contains much overlapping data with a non-normalized correlation analysis between two events, since lack of normalization means that two events of different amplitudes would show poor correlation; normalizing the correlation analysis would reduce the data overlap.

One potential concern of overdetection analysis is that it may incorrectly mark events as overdetections due to characteristics that form apparent patterns during actual arrhythmias. For example, by their very natures, polymorphic tachyarrhythmia and ventricular fibrillation can be random, and misidentification of overdetection could delay or impede identification of treatable arrhythmia. For this reason, the tendency is to select the thresholds for various characteristics conservatively to avoid over-marking overdetection. In the example of FIG. 11, this challenge may be overcome. In the example, to identify overdetection, at least two of the set of events 250 have to be marked as overdetections using at least two different characteristics. In the illustration, event [n−2] is marked as a likely overdetection using a dynamic correlation analysis (block 256), and event [n−4] is marked as a likely overdetection using a static correlation analysis (block 254). Because two events in the queue are marked as overdetections, using two different characteristics, the analysis can confidently mark each of [n−2] and [n−4] as overdetections.

In the example of FIG. 11, as shown in the chart below, there may be two separate paths to identifying overdetection—following a first path, an individual detected event can be marked as an overdetection by reference to the event and one preceding or following event, or the event and each of the preceding and following events; following a second path, an amalgam approach looks for multiple individual events in a queue of several events (in the example, eight events) showing, using at least two separate characteristics, overdetection by reference to one or both of the preceding and/or following events. The "individual" path can use strict rules but relies on a single method and marks an individual event, while the amalgam path applies looser rules for pattern identification but requires multiple events and/or multiple methods.

In an illustrative example, the following thresholds are used to categorize each event for each Characteristic:

| | Characteristic | | | | | | |
|---|---|---|---|---|---|---|---|
| | Intervals | | Static Corr. | | Dynamic Corr. | | Width | |
| Category | Short | Long | Low | High | Low | High | Wide | Narrow |
| Individual | W | X | 25% | 60% | 25% | 60% | A | B |
| Amalgam | Y | Z | 30% | 45% | 30% | 45% | C | D |

Where "Average Interval" is the average of a previous number of measured intervals between detected events and:
W=Average Interval Minus 35
milliseconds X=Average
Interval Plus 35 milliseconds Y=
Average Interval Minus 20
milliseconds Z=Average Interval
Plus 20 milliseconds
Also, "Estimated Width" is a width calculated similar to that described above for FIG. 6 and: A=Estimated Width Plus 65 milliseconds B=Estimated Width Plus 25 milliseconds C=Estimated Width Plus 50 milliseconds D=Estimated Width Plus 30 milliseconds These thresholds for categories are merely illustrative of one example, and other thresholds can be used instead. As can be seen from these numeric examples, the "Individual" approach calls for higher/lower correlation, shorter/longer intervals, and wider/narrower width limits, with a larger "in-between" space provided than in the Amalgam approach in this example.

In these examples, one goal is to combine different methods to create minimal data redundancy, for example, the following combinations create minimal data redundancy: Interval analysis and morphology;
   Correlation to a static template and correlation to a dynamic template;
   Interval analysis and Frequency content;
   Amplitude and normalized correlation waveform analysis; and
   Wavelet coefficient analysis (or other signal decomposition analysis) and Correlation Waveform Analysis.

For this list of factors, overdetection analysis may apply by looking for alternating patterns, for example, patterns of long-short-long-short intervals, high-low-high-low morphology correlation, alternating patterns of frequency content for individual events, high-low-high-low patterns of amplitude, and alternating patterns of wavelet coefficient (or other signal decomposition) results. For example, if wavelet analysis uses wavelet coefficients W(1) . . . W(n), wavelet decomposition can provide an ordered series of these components; to identify an alternating pattern, one may look for whether the top three (or other number) factors of the ordered series alternate from event to event to find an alternating pattern. U.S. Pat. No. 6,393,316 is incorporated herein by reference for showing examples of wavelet analysis as applied to a cardiac system. For another example, frequency content may be used by performing a transform of the cardiac signal of one detected cardiac cycle into the frequency domain and establishing a set of frequency peaks or estimate of frequency content, and looking for alternating patterns of transform peaks from one event to the next. Peaks likely caused by noise can be ignored in the frequency transform analysis.

One difficulty that arises when combining multiple methods is the need for specific outcomes and prioritization. For example, if static correlation analysis suggests alternating pattern indicating overdetection, but frequency content from beat to beat is very consistent (not indicating overdetection), which of these two factors "Wins" and, if one wins over the other, then why observe both? One answer to is to use three or more factors in combination and rely on a majority rule. Another answer is to define specific characteristics with priority within certain ranges.

An example using three factors in combination would be as follows: if observing each of static template morphology matching, frequency content, and dynamic template morphology, if two of three indicate overdetection, then overdetection is identified, regardless of the result of the third analysis. An example giving certain characteristics priority within certain ranges would identify a rate below a set limit (140 bpm, for example) never indicates overdetection, while above that threshold, the rate is no longer primary, and other factors can be considered. Where combinations of factors can be considered, there may be tiers, for example, with a first tier in which narrow limits apply to allow overdetection identification using a single factor, and a second tier in which wider limits apply to allow overdetection identification if agreement of several factors, each in the wider limit range, occurs. In a further example, narrow limits may identify overdetection by analysis of 1 to 3 events, while the wider limits can be used to identify overdetection by analysis of 3 to 5 (or more) events, as shown above.

In another example, when one characteristic is identified as suggesting overdetection, the other characteristics may be reviewed to look for indications that ordinary detection is occurring. For example, a long-short-long Interval sequence suggests overdetection, but if each of the events is characterized as "Wide," then overdetection may not be occurring. In such an example, the identification of long-short-long Interval sequences, with all events being Wide and no events having high static or dynamic correlation would suggest that the interval pattern is simply random and that no overdetection has actually taken place. Such contrasting outcomes create a conflict that can be resolved, for example, by reference to a third feature or by reference to which of two contrasting features has greater confidence (how "wide" the events are, for example). Such conflict may also be resolved by ignoring intervals around the suspected overdetection for which conflict exists, as well as the detection itself, for use in rate and/or other analysis directed at therapy decisions.

Figure 12:
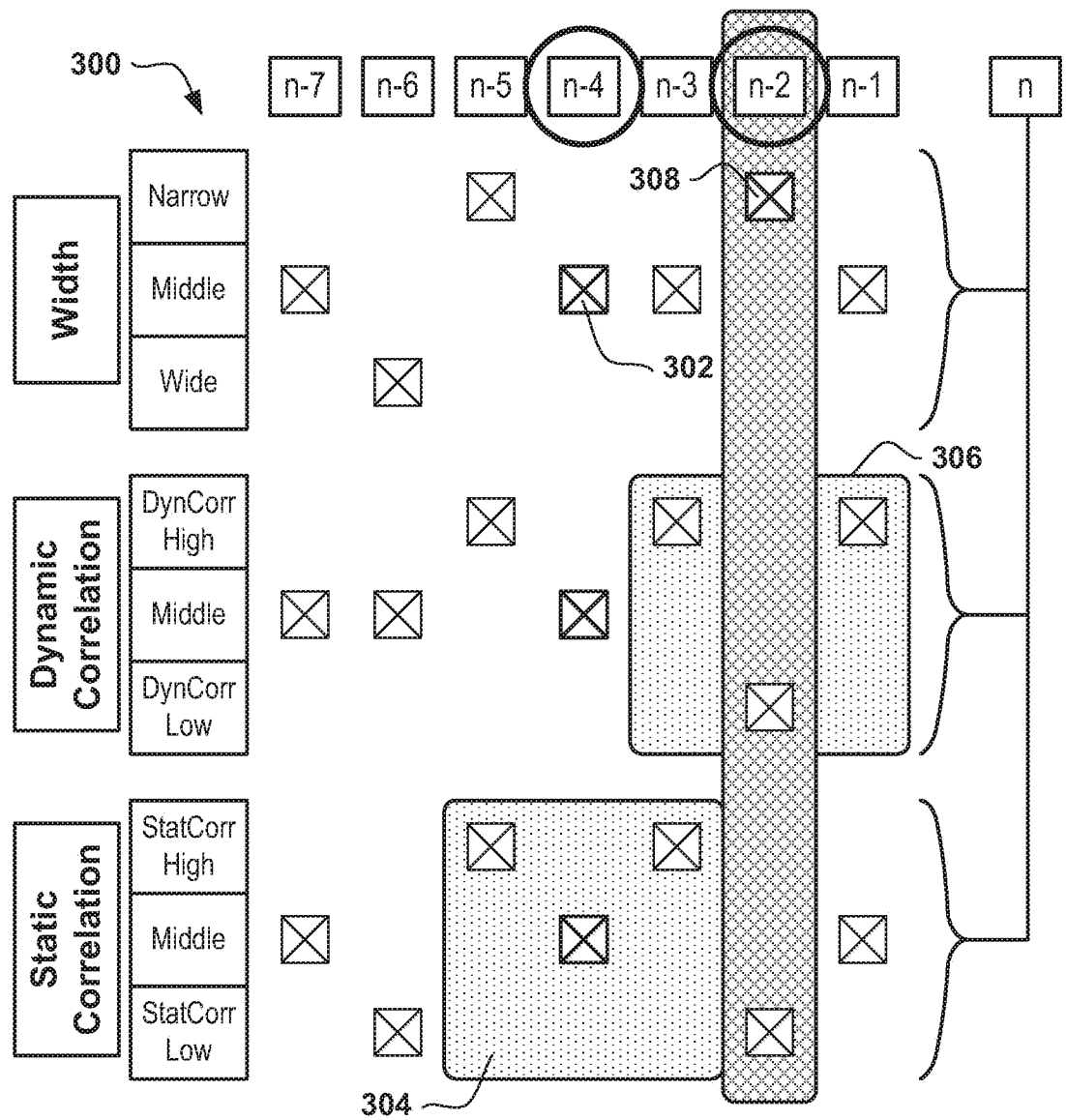

FIG. 12 illustrates another analysis method. A set of events is shown at 300 from event [n] to event [n−7]. Analytics for the events 300 are displayed including Width (Narrow-Middle-Wide), Dynamic Correlation (High-Middle-Low) and Static Correlation (High-Middle-Low). As shown at 302, the [n−4] event has a "middle" width; that is, it is not sufficiently narrow to clearly indicate it is a normal R-wave, but not so wide as to be particularly unusual. Block 304 shows a pattern of High-Middle-High for Static Correlation outputs for events [n−3] to [n−5], and Block 306 shows a pattern of High-Low-High for Dynamic Correlation outputs for events [n−1] to [n−3]. In some embodiments, this combination would lead to marking of events [n−2] and [n−4] as overdetections, due to a persistent pattern suggesting overdetection across events [n−1] to [n−5]. However, as highlighted at 308, the [n−2] event has a narrow width. This suggests that [n−2] is cardiac in origin. Given the narrow width, identification of overdetection is inhibited in this example. In short, the example of FIG. 12 demonstrates an embodiment in which narrow width takes priority over the other factors under consideration.

FIG. 13 illustrates another analysis method. A set of events is shown at 400, again from event [n] to event [n−7], with several event categories marked as A, B, C and D. A and B are provided as first and second opposing categories, such as Wide/Narrow, High/Low Correlation, or Long/Short Interval. C is the middle category that represents neither A nor B, and D indicates that some other method of overdetection identification has identified an overdetection. The marking of the events indicates two triplets—ABA 402 and ADA 404. This indicates that a pattern of multiple likely overdetections has appeared in the set of eight detected events 400.

The application of a set of rules is provided in the lower portions of the drawing. In the example, several combinations of triples are sought, including two ABA triples 410, an ADA and an ABA triple 412, two BAB triples 420, or a BDB and BAB triple 422. If either of 410 or 412 is met, then the analysis determines whether there are any BB pairs 414, which would suggest that the type of overdetection sought using A as the non-overdetected events is unlikely. If there are no BB pairs, then the method finds overdetection 416 and marks each B detection in any ABA triple as an overdetection. If one or more BB pairs exist at 414, the condition fails and the method concludes there is no overdetection 418.

If either of conditions 420 or 422 is found, the method checks for any AA pairs at 424. If there are no AA pairs in combination with meeting one of conditions 420, 422, then the method determines that overdetection has taken place 416, and will mark the A events in any BAB triple as overdetections. If condition 424 fails, again, the method finds no additional overdetection using the AB categories, as indicated at 418. In the method demonstrated by FIG. 13, no distinction is made between "ABA" and "BAB" suggesting that either of these alternating patterns can indicate overdetection; in other examples, only one of the two alternating patterns is allowed to suggest overdetection; in yet other examples, which of ABA or BAB is considered indicative of overdetection depends on the nature of the "D" overdetection analysis. For example, if "D" is an overdetection based on static correlation, then (in on embodiment) from the perspective of width, a narrow-wide-narrow pattern would indicate overdetection but not a wide-narrow-wide pattern, while if "D" is an overdetection based on alternating intervals, either of narrow-wide-narrow and wide-narrow-wide patterns of width could indicate overdetection.

Various analyses can feed the categories referenced in FIG. 13. Examples given above include intervals, static or dynamic correlation analysis (whether normalized to amplitude or not), frequency analysis, principal components or wavelet transform analysis, width, and any other suitable feature, as well as patterns, whether long or short, for these features. Another notable category is total energy, for example, the root-mean-square signal amplitude during a window associated with a detected event may be captured and analyzed in absolute or comparative terms. Variations in total energy may suggest that not all detected events are of the same type (i.e. QRS complexes followed by T-waves); consistent total energy suggests that each detected event is of the same nature, whether of arrhythmia or normal rhythm; total energy may be compared to total area by summing the signal amplitudes relative to baseline during a window and comparing to the root mean square of amplitudes during a sensing window, providing an indication of how biphasic the signal is. If detections go from monophasic to biphasic in a patterned manner, this may indicate overdetection, since the detections are unlike one another in a fashion that is not apparently random.

Figure 14:
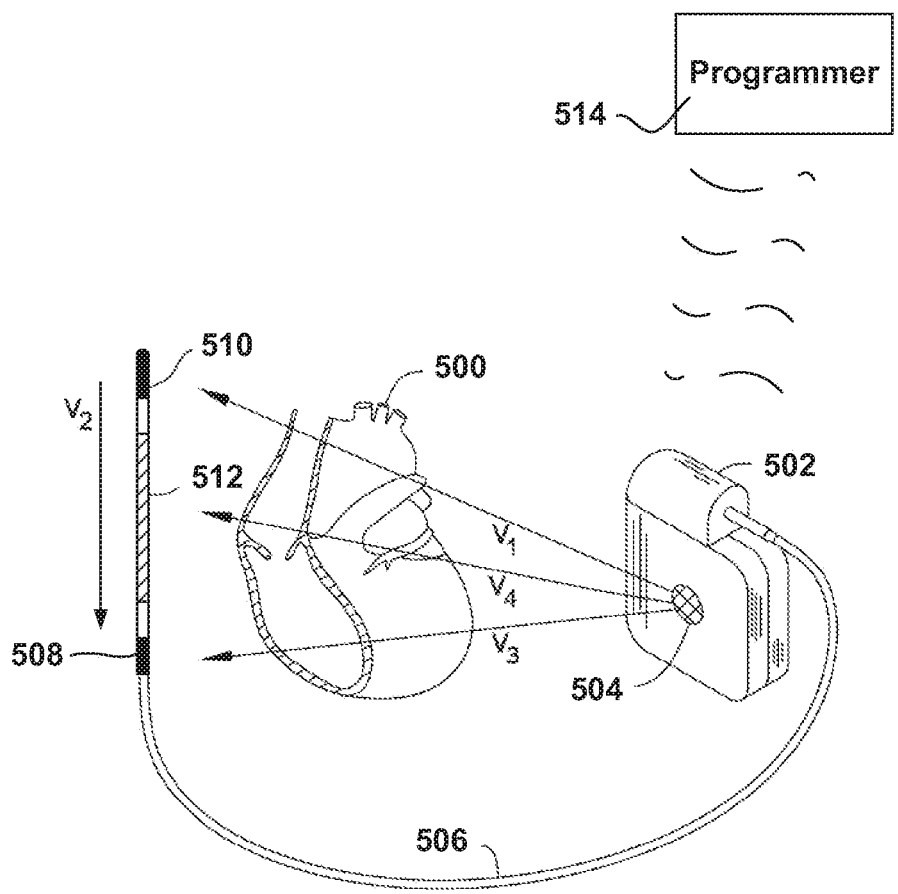
FIG. 14 shows an illustrative implantable cardiac device.

FIG. 14 shows an illustrative implantable cardiac stimulus device. A subcutaneous-only system is represented relative to a patient's heart 500, with a canister 502 having a canister electrode 504 (the canister electrode 504 may be a separate element or it may comprise all, a region, or a surface of the housing of the canister 502). The canister 502 is coupled to a lead 506 that includes distally located electrodes 508, 510, 512. The multiple electrodes 504, 508, 510, 512 provide multiple available sensing vectors and/or multiple available shock vectors. The system may communicate with an external programmer 514, wherein the programmer 514 can be used to set system parameters, monitor system functions, update software, and retrieve diagnostic or history information for use by an operator of the programmer 514.

In the system shown in FIG. 14, subcutaneous implantation is represented, and the lead 506 does not contact or enter the heart 500 and/or patient vasculature. The system may be implanted over the ribcage of the patient. One example places the canister 502 near the left axilla with the lead 506 extending along the inframammary crease toward the xiphoid and then along the sternum. Other examples may place the canister 502 in an anterior, more superior position, either below or above the pectoral muscles. The lead 506 may instead extend laterally and/or posteriorly. Multiple leads can be provided. The lead 506 may instead be advanced toward the posterior of the patient, such to a location adjacent the spine, or the lead may be advanced across the sternum to the right side of the patient's chest.

In other examples, one or more transvenous leads may extend into the patient's vasculature, with one or more electrodes attached to or residing in the heart 500. Yet other examples may use one or more epicardial electrodes attached to the exterior of the heart 500. Rather than a canister 502 over the ribs of the patient, the canister 502 may be placed abdominally or may be specially designed for emplacement in the vasculature of the patient or at any suitable location. Designs and materials for the lead 506 and canister 502 may vary widely, and may include such examples as stainless steel, titanium, silver, gold, any number of well known alloys, etc. for the electrodes, conductors or canister, with various suitable polymers, ceramics, oxides or coatings available for use to shield, protect or secure elements of the system.

Figure 15:
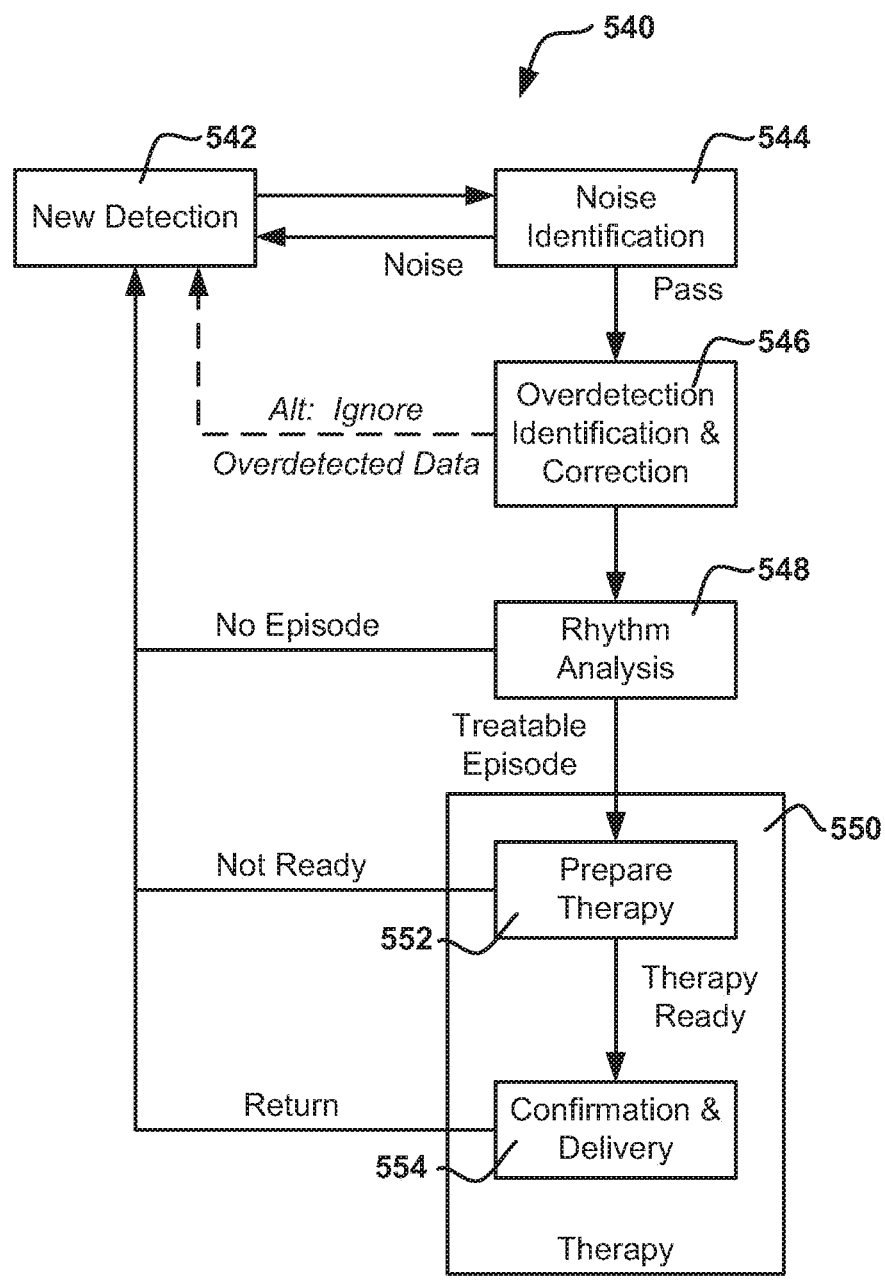
FIG. 15 illustrates a method of operating an implantable cardiac device.

FIG. 15 illustrates, in block form, a method of operating an implantable cardiac stimulus device (ICSD). The method 540 is generally driven by identification of a new detected event by the ICSD, indicated as a new detection 542. Each new detection 542 represents a likely cardiac event, implying that a new cardiac cycle has been observed. Illustrative examples of cardiac event detection are shown in US Patent Application Publication Number 2009-0228057, titled ACCURATE CARDIAC EVENT DETECTION IN AN IMPLANTABLE CARDIAC STIMULUS DEVICE, the disclosure of which is incorporated herein by reference.

The method 540 then checks the new detection 542 using noise detection 544 and overdetection identification and correction 546. These processes at 544 and 546 can analyze individual detections and/or small groups of detections to ensure accurate detection and analysis.

If noise identification 544 reveals that a new detection is likely caused by noise, then the method 540 can return to block 542 and await a next detection. Illustrative examples of noise detection can be found, for example, in U.S. Pat. No. 7,248,921, titled METHOD AND DEVICES FOR PERFORMING CARDIAC WAVEFORM APPRAISAL, and/or U.S. Provisional Patent Application Ser. No. 61/255,253, and U.S. patent application Ser. No. 12/913,647, each titled ADAPTIVE WAVEFORM APPRAISAL IN AN IMPLANTABLE CARDIAC SYSTEM, the disclosures of which are incorporated herein by reference.

If overdetection identification and correction 546 reveals that an overdetection has occurred, the method may continue to rhythm analysis 548 or, alternatively, may return to block 542 to await a next detection. Some examples are shown throughout the present disclosure. Some additional illustrative examples of overdetection identification and correction are shown, for example, in US Patent Application Publication Number 2009-0259271, titled METHODS AND DEVICES FOR ACCURATELY CLASSIFYING CARDIAC ACTIVITY, US Patent Application Publication Number US 2010-0004713 A1, also titled METHODS AND DEVICES FOR ACCURATELY CLASSIFYING CARDIAC ACTIVITY, and U.S. Provisional Patent Application Ser. No. 61/255,249 and U.S. patent application Ser. No. 12/913,642, each titled METHODS AND DEVICES FOR IDENTIFYING OVERDETECTION OF CARDIAC SIGNALS, the disclosures of which are incorporated herein by reference.

Once the individual detections have been analyzed for noise and overdetection purposes, the illustrative method 540 continues to Rhythm Analysis, as shown at 548. Rhythm analysis 548 determines whether a treatable episode of identified arrhythmia is ongoing. If there is no treatable episode, the method 540 returns to block 542 to await the next detection. If there is a treatable episode ongoing, the method continues to Charging/Therapy block 550. Some examples of Rhythm analysis 548 appear in U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR; U.S. Pat. No. 7,330,757, titled METHOD FOR DISCRIMINATING BETWEEN VENTRICULAR AND SUPRAVENTRICULAR ARRHYTHMIAS; US Patent Application Publication Number 2006-0167503, titled METHOD FOR ADAPTING CHARGE INITIATION FOR AN IMPLANTABLE CARDIOVERTER-DEFIBRILLATOR; and US Patent Application Publication Number 2009-0259271, titled METHODS AND DEVICES FOR ACCURATELY CLASSIFYING CARDIAC ACTIVITY, the disclosures of which are incorporated herein by reference.

If a treatable episode has been found, the method continues at block 550. The method then includes preparing for therapy, as shown at 552. In some devices/examples, therapy delivery is performed by first preparing to deliver therapy by charging an output capacitor to a desired voltage/energy level, as is known in the art. The prepare therapy block 552 allows cycling through the rest of the analysis 550 in an iterative manner during charging or other therapy preparation. For some systems and therapies, block 552 may be omitted, for example if pacing therapy can be applied without requiring capacitor charging. In other systems, block 552 may enforce a minimum delay period (or number of detected events) to confirm persistence of treatable arrhythmia before therapy is delivered. Confirmation of therapy may be as shown in US Patent Application Publication Number 2010-0331904, titled ADAPTIVE CONFIRMATION OF TREATABLE ARRHYTHMIA IN IMPLANTABLE CARDIAC STIMULUS DEVICES, the disclosure of which is incorporated herein by reference.

When the system is prepared to deliver therapy at 552, confirmation and therapy delivery are performed, as shown at 554. Confirmation is an optional step that can be included to ensure that therapy continues to be indicated throughout and beyond the end of charging. Therapy may be delivered synchronously or asynchronously, using methods known in the art. Some illustrative devices and methods related to confirmation and delivery are shown in US Patent Application Publication Number 2009-0198296, titled ADAPTIVE SHOCK DELIVERY IN AN IMPLANTABLE CARDIAC STIMULUS DEVICE; US Patent Application Publication Number 2009-0187227, titled DATA MANIPULATION FOLLOWING DELIVERY OF A CARDIAC STIMULUS IN AN IMPLANTABLE CARDIAC STIMULUS DEVICE; U.S. patent application Ser. No. 12/826,241, titled ADAPTIVE CONFIRMATION OF TREATABLE ARRHYTHMIA IN IMPLANTABLE CARDIAC STIMULUS DEVICES; US Patent Application Publication Number 2006-0167503, titled METHOD FOR ADAPTING CHARGE INITIATION FOR AN IMPLANTABLE CARDIOVERTER-DEFIBRILLATOR; and US Patent Application Publication Number US 2010-0094369 A1, titled METHODS AND DEVICES FOR ACCURATELY CLASSIFYING CARDIAC ACTIVITY, the disclosures of which are incorporated herein by reference.

The above examples for each of steps 542, 544, 546, 548, 550, 552 and 554 are merely illustrative, and other suitable methods can be used as well.

While the above is presented in the context of an implantable cardiac stimulus device, other implantable systems may also incorporate these methods. One example may be an implantable loop recorder (ILR). Rather than a therapy decision, a decision to store certain data for later upload may be made in an ILR. For example, some implantable monitors are configured to retain data only when a decision is made by the implant that abnormal and/or potentially malignant activity is occurring. In some further embodiments, data may be stored when captured data requires correction due to overcounting, in order that the sensing and detection characteristics of the system and/or implant location may be analyzed to determine its suitability for long-term use. A monitoring system may also output a warning if a malignant condition is identified, for example by annunciation to the implantee or by communication with an external alert system.

The above illustrative examples may be embodied in many suitable forms. Some embodiments include methods incorporating one or more of the above features/sub-methods in various combinations. Some embodiments are devices adapted to perform one or more of the methods discussed above and/or a system including implantable devices and associated external programming devices. Some embodiments are tangible media, such as magnetic, electric, or optical storage media, having fixed thereon in suitable form controller readable instruction sets. Some embodiments are or include controllers or microcontrollers associated with stored instruction sets for directing operations of various components in a device in accordance with one or more methods. Some aspects of various embodiments may be embodied in dedicated hardware such as analog or digital application specific integrated circuits, or other logic, memory or control circuits.

The design details of operational circuitry for an implantable system may vary widely. Briefly, an illustrative example may make use of a microcontroller-driven system which can include an input switch matrix for selecting one or more signal vectors as a sensing vector. The switch matrix in this example is coupled to filtering circuitry and at least one input amplifier. Filtering may include high pass, low pass and/or bandpass or bandstop filtering. The amplified, filtered signal in the example is provided to analog-to-digital conversion circuitry, which may include baseline zeroing filters as well. Additional filtering of the incoming signal may be performed in the digital domain including high pass, low pass and/or bandpass or bandstop filtering. In the example, the incoming signal is then analyzed by the microcontroller and any associated logic or other circuitry, including memory. Some embodiments may also include dedicated hardware for peak or event detection and amplitude measurement, or for morpohology analysis such as comparison to a template, which may take numerous forms such as correlation waveform analysis, difference of area analysis, principle component analysis and/or wavelet transform analysis.

In several illustrative examples, upon identification of a rhythm that indicates therapy, a charging operation is undertaken to charge one or more high-power capacitors to suitable levels for therapy. A charging sub-circuit may take any suitable form. One example uses a flyback transformer circuit, a structure well known in the art. Any process and/or circuit that enables relatively low voltage batteries to charge capacitors to relatively high voltages may be used. Some systems also perform annunciation and/or communication in response to detected malignancy, for example, to alert the implantee or a medical facility that therapy is imminent or intervention is needed. Alternatively, some examples provide therapies that do not require charging circuitry, for example, pacing including without limitation anti-tachycardia pacing.

The device may further include output circuitry comprising, for example, an output H-bridge or modification thereof for controlling output polarity and pulse duration. Control circuitry associated with the H-bridge may be included, for example, to monitor or control current levels for constant current output signals, voltage levels or for performing diagnostic functions including system, lead, circuit and/or component integrity checks. The circuitry may be housed in a hermetically sealed canister made of any suitable material.

While voltage and power levels may vary, in one example, an implantable subcutaneous cardioverter-defibrillator includes charging circuitry and capacitors sized to receive and hold energy at 1350 volts, and uses output circuitry/controller that provide an output that yields a delivered charge of 80 Joules in a biphasic waveform with about 50% tilt. Other voltage, energy and tilt levels (higher and/or lower), and other waveforms may be used, and the load can varies in response to electrode position and physiology. Illustrative ranges for high amplitude therapy may include 3-2500 volts, 1-140 Joules, etc. The configuration of output waveform need not be static, and any suitable methods/configurations for providing the output may be used (including, without limitation, pre-shock waveforms, monophasic or multiphasic waveforms, adaptation or progression of therapy energy or voltage level, changes in duration or polarity, fixed current or fixed voltage, etc.) Some embodiments use tiered therapies including anti-tachycardia-pacing as well as cardioversion and/or defibrillation stimuli.

Analysis may take several forms in terms of the inputs taken. For example, a multiple sensing electrode system may be configured to select a default sensing vector and use the default vector throughout analysis. Other systems may prioritize vectors for use in tiered analysis in which one vector is analyzed after another. Yet other systems may analyze multiple vectors simultaneously, for example, using multiple channels to reach separate analytical results, using one channel to establish markers for use in analyzing data in a second channel (for example, separate rate and morphology channels may be used), or combining two channels of data.

One example, (A), takes the form of an implantable cardiac stimulus device comprising a plurality of electrodes configured for implantation into a patient and operational circuitry electrically coupled to the electrodes, wherein the operational circuitry is configured to perform a method comprising: sensing a signal with the electrodes; detecting events from the sensed signal; estimating an average width of a set of the detected events; establishing parameters for characterizing detected events as wide and narrow using the average width; capturing a series of detected events; characterizing the series of detected events as wide or narrow; identifying a qualifying narrow-wide-narrow sequence of detected events; and determining that the wide event of a narrow-wide-narrow sequence is an overdetected event. In a further aspect of (A), the operational circuitry is configured such that the step of establishing parameters for characterizing detected events as wide and narrow comprises adding a fixed window value to the average width to calculate a QWCLimit parameter; and the step of characterizing the series of detected events as wide or narrow estimating the width of each of the series of detected events, comparing the estimated width to QWCLimit and: characterizing events having a width that is less than QWCLimit as Narrow; characterizing events having a width that is greater than QWCLimit plus a buffer value as Wide; or for an event having a width that is greater than QWCLimit but not greater than QWCLimit plus the buffer value, characterizing the event as Wide if the immediately preceding event was Wide and, otherwise, characterizing the even at Narrow. In another further aspect of (A), operational circuitry is configured such that the step of identifying a qualifying narrow-wide-narrow sequence of detected events requires both the Narrow events in the sequence to have a width that is less than QWCLimit. In another further aspect of (A), the operational circuitry is further configured to perform the following steps: if an overdetected event occurs, correcting data relating to the overdetected event; and using the corrected captured data to analyze the patient's cardiac rhythm; wherein the operational circuitry is configured such that the step of using the corrected data to analyze the patient's cardiac rhythm includes characterizing the patient's cardiac rhythm as either treatable or not treatable and, if the patient's cardiac rhythm is characterized as treatable, then the method further comprises delivering therapy to the patient using at least a pair of the plurality of electrodes. In another further aspect of (A), the operational circuitry is configured such that the step of correcting data related to the overdetected event includes: identifying a preceding interval between the overdetected event and an immediately previous detected event; and identifying a trailing interval between the overdetected event and an immediately following detected event; combining the preceding interval with the trailing interval to form a combined interval; and estimating a cardiac rate for the patient using at least the combined interval.

In a further aspect of (A), the operational circuitry is further configured to perform the following steps: if an overdetected event occurs, correcting captured data relating to the overdetected event; and using the corrected captured data to analyze the patient's cardiac rhythm; wherein the operational circuitry is configured such that the step of using the corrected data to analyze the patient's cardiac rhythm includes characterizing the patient's cardiac rhythm as either treatable or not treatable and, if the patient's cardiac rhythm is characterized as treatable, then the method further comprises delivering therapy to the patient using at least a pair of the plurality of electrodes.

In a further aspect of (A), the operational circuitry is configured such that the step of correcting data related to the overdetected event includes: identifying a preceding interval between the overdetected event and an immediately previous detected event; and identifying a trailing interval between the overdetected event and an immediately following detected event; combining the preceding interval with the trailing interval to form a combined interval; and estimating a cardiac rate for the patient using at least the combined interval.

Another example (B) includes a method of analyzing cardiac signal data in an implantable medical device comprising a plurality of electrodes configured for implantation into a patient and operational circuitry electrically coupled to the electrodes, the method being performed by the operational circuitry using the electrodes, the method comprising: sensing a signal with the electrodes; detecting events from the sensed signal; estimating an average width of a set of the detected events; establishing parameters for characterizing detected events as wide and narrow using the average width; capturing a series of detected events; characterizing the series of detected events as wide or narrow; identifying a qualifying narrow-wide-narrow sequence of detected events; and determining that the wide event of a narrow-wide-narrow sequence is an overdetected event. In a further aspect of (B), the step of establishing parameters for characterizing detected events as wide and narrow comprises adding a fixed window value to the average width to calculate a QWCLimit parameter; and the step of characterizing the series of detected events as wide or narrow estimating the width of each of the series of detected events, comparing the estimated width to QWCLimit and: characterizing events having a width that is less than QWCLimit as Narrow; characterizing events having a width that is greater than QWCLimit plus a buffer value as Wide; or for an event having a width that is greater than QWCLimit but not greater than QWCLimit plus the buffer value, characterizing the event as Wide if the immediately preceding event was Wide and, otherwise, characterizing the even at Narrow. In another further aspect of (B), the step of identifying a qualifying narrow-wide-narrow sequence of detected events requires both the Narrow events in the sequence to have a width that is less than QWCLimit. In another further aspect of (B), the method also includes if an overdetected event occurs, correcting data relating to the overdetected event; using the corrected captured data to analyze the patient's cardiac rhythm including characterizing the patient's cardiac rhythm as either treatable or not treatable; and, if the patient's cardiac rhythm is characterized as treatable, delivering therapy to the patient using at least a pair of the plurality of electrodes. In another further aspect of (B), the step of correcting data related to the overdetected event includes: identifying a preceding interval between the overdetected event and an immediately previous detected event; identifying a trailing interval between the overdetected event and an immediately following detected event; adding the preceding interval and the trailing interval into a combined interval; and estimating a cardiac rate for the patient using at least the combined interval.

In a further aspect of (B), the method also includes, if an overdetected event occurs, correcting captured data relating to the overdetected event; using the corrected captured data to analyze the patient's cardiac rhythm including characterizing the patient's cardiac rhythm as either treatable or not treatable; and, if the patient's cardiac rhythm is characterized as treatable, delivering therapy to the patient using at least a pair of the plurality of electrodes. In another further aspect of (B), the step of correcting data related to the overdetected event includes: identifying a preceding interval between the overdetected event and an immediately previous detected event; identifying a trailing interval between the overdetected event and an immediately following detected event; adding the preceding interval and the trailing interval into a combined interval; and estimating a cardiac rate for the patient using at least the combined interval.

Another example takes the form of an implantable cardiac device comprising a plurality of electrodes configured for implantation into a patient and operational circuitry electrically coupled to the electrodes, wherein the operational circuitry is configured to perform a method comprising: sensing a signal with the electrodes; detecting events from the sensed signal; for each of several characteristics, categorizing the detected events; observing alternating categorizations of the detected events within the several characteristics and combining categorizations from separate characteristics to identify overdetection using at least two characteristics that each show alternating categories in a predetermined manner. In a further example, the characteristics include at least width and detection intervals. In another further example, the characteristics include at least width and correlation. In yet another further example, the characteristics include at least width, detection intervals, and correlation. In these further examples, correlation may be calculated relative to a dynamic template or a static template.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable cardiac device comprising a plurality of electrodes configured for implantation into a patient for at least sensing cardiac signals and operational circuitry electrically coupled to the electrodes, wherein the operational circuitry is configured to perform a method comprising:
   sensing a signal with the electrodes;
   detecting events from the sensed signal, the detected events being separated by intervals;
   capturing a series of detected events;
   characterizing the series of detected events as wide or narrow;
   identifying a qualifying narrow-wide-narrow sequence of detected events; and
   determining that the wide event of the qualifying narrow-wide-narrow sequence is an overdetected event;
   wherein the operational circuitry is configured to calculate a cardiac rate for the patient using intervals between detected events which are not determined to be overdetections.

2. An implantable cardiac device as in claim 1, wherein the operational circuitry is configured such that characterizing the series of detected events as wide or narrow includes estimating the width of each of the series of detected events, comparing the estimated width to a width threshold and:

characterizing events having a width that is less than the width threshold as narrow;

characterizing events having a width that is greater than the width threshold plus a predefined buffer value as wide; and characterizing events having a width greater than the width threshold and less than the width threshold plus the predefined buffer value as Wide if the immediately preceding event was Wide and, otherwise, characterizing the event as Narrow.

3. An implantable cardiac device as in claim 2, wherein the operational circuitry is configured such that the step of identifying a qualifying narrow-wide-narrow sequence of detected events requires both the narrow events in the sequence to have a width that is less than the width threshold.

4. An implantable cardiac device as in claim 1, wherein the operational circuitry is further configured to perform the following steps:

if an overdetected event occurs, correcting data relating to the overdetected event; and using the corrected data to analyze the patient's cardiac rhythm;

wherein the operational circuitry is configured such that the step of using the corrected data to analyze the patient's cardiac rhythm includes characterizing the patient's cardiac rhythm as either treatable or not treatable and, if the patient's cardiac rhythm is characterized as treatable, then the device is further configured to deliver therapy using at least a pair of the plurality of electrodes.

5. An implantable cardiac device as in claim 1, wherein the operational circuitry is further configured to perform the following steps:

if an overdetected event occurs, correcting captured data relating to the overdetected event; and using the corrected captured data to analyze the patient's cardiac rhythm;

wherein the operational circuitry is configured such that the step of using the corrected data to analyze the patient's cardiac rhythm includes characterizing the patient's cardiac rhythm as either treatable or not treatable and, if the patient's cardiac rhythm is characterized as treatable, then the operational circuitry is configured to deliver therapy to the patient using at least a pair of the plurality of electrodes.

6. An implantable cardiac device comprising a plurality of electrodes configured for implantation into a patient for at least sensing cardiac signals and operational circuitry electrically coupled to the electrodes, wherein the operational circuitry is configured to perform a method comprising:

sensing a signal with the electrodes;

detecting events from the sensed signal, the detected events being separated by intervals;

analyzing the detected events to develop a set of several characteristics of the detected events;

for each of the set of several characteristics, categorizing the detected events;

observing alternating categorizations of the detected events within the several characteristics; and combining categorizations from two separate characteristics to identify overdetections within the detected events using at least two characteristics that each show alternating categories in a predetermined manner;

wherein the operational circuitry is configured to calculate a cardiac rate for the patient using intervals between detected events which are not determined to be overdetections.

7. An implantable cardiac device as in claim 6, wherein:
the characteristics include at least width and correlation;
the categorizations include:
for width, wide and narrow; and
for correlation, high and low; and
the combining step includes finding a sequence of narrow-wide-narrow widths for a first series of three detected events, and finding a sequence of high-low-high correlations for a second series of three detected events, the first series including at least one detected event that is not in the second series.

8. An implantable cardiac device as in claim 7 wherein the correlation is calculated as correlation to a stored static template.

9. An implantable cardiac device as in claim 7 wherein the correlation is a dynamic correlation.

10. An implantable cardiac device as in claim 6, wherein:
the characteristics include at least width and detection intervals;
the categorizations include:
for width, wide and narrow; and
for detection intervals, long and short; and
the combining step includes finding a sequence of narrow-wide-narrow widths for a first series of three detected events, and finding a sequence of long-short-long detection intervals for a second series of three detected events, the first series including at least one detected event that is not in the second series.

11. An implantable cardiac device as in claim 6, wherein:
the characteristics include at least correlation and detection intervals;
the categorizations include:
for detection intervals, long and short; and
for correlation, high and low; and
the combining step includes finding a sequence of long-short-long detection intervals for a first series of three detected events, and finding a sequence of high-low-high correlations for a second series of three detected events, the first series including at least one detected event that is not in the second series.

12. An implantable cardiac device as in claim 11 wherein the correlation is calculated as correlation to a stored static template.

13. An implantable cardiac device as in claim 11 wherein the correlation is a dynamic correlation.

14. An implantable cardiac device comprising a plurality of electrodes configured for implantation into a patient and operational circuitry electrically coupled to the electrodes, wherein the operational circuitry is configured to perform a method comprising:

a) sensing a signal with the electrodes;
b) detecting events from the sensed signal, the detected events being separated by intervals;
c) analyzing the detected events to develop a set of several characteristics of the detected events;
d) using a first characteristic of the set of several characteristics, identifying an alternating pattern indicating that a particular one of the set of detected events likely resulted from overdetection;
e) reviewing a second characteristic of the set of several characteristics and determining that the particular one of the set of detected events is not an overdetection notwithstanding step d); and f) using selected ones of the set of detected events, including the particular one of the set of detected events analyzed in steps d) and e), to estimate a cardiac rate.

15. An implantable cardiac device as in claim 14, wherein the first of the set of several characteristics is correlation relative to a template, and the second of the set of several characteristics is detected event width.

16. An implantable device as in claim 15, wherein the correlation is a static correlation.

17. An implantable device as in claim 15, wherein the correlation is a dynamic correlation.

18. An implantable cardiac device as in claim 14, wherein the first of the set of several characteristics is interval duration, and the second of the set of several characteristics is detected event width.

19. An implantable cardiac device as in claim 14, wherein the first of the set of several characteristics is interval duration, and the second of the set of several characteristics is dynamic correlation relative to a template.

20. An implantable cardiac device as in claim 14, wherein the first of the set of several characteristics is interval duration, and the second of the set of several characteristics is static correlation relative to a template.

\* \* \* \* \*